United States Patent
Kim

(10) Patent No.: US 12,285,245 B2
(45) Date of Patent: Apr. 29, 2025

(54) ELECTRONIC DEVICE COMPRISING ULTRASONIC DEVICE AND PPG SIGNAL ACQUISITION METHOD THEREOF

(71) Applicant: Samsung Electronics Co., Ltd., Suwon-si (KR)

(72) Inventor: Jinho Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 82 days.

(21) Appl. No.: 18/151,882

(22) Filed: Jan. 9, 2023

(65) Prior Publication Data

US 2023/0157561 A1    May 25, 2023

Related U.S. Application Data

(63) Continuation of application No. PCT/KR2021/007409, filed on Jun. 14, 2021.

(30) Foreign Application Priority Data

Jul. 13, 2020  (KR) .................. 10-2020-0086000

(51) Int. Cl.
*A61B 5/024*    (2006.01)
*A61B 5/00*     (2006.01)
*A61B 8/02*     (2006.01)

(52) U.S. Cl.
CPC ...... *A61B 5/02427* (2013.01); *A61B 5/02405* (2013.01); *A61B 5/6898* (2013.01);
(Continued)

(58) Field of Classification Search
CPC ............ A61B 5/02427; A61B 5/02405; A61B 5/6898; A61B 5/7221; A61B 5/7455;
(Continued)

(56) References Cited

U.S. PATENT DOCUMENTS 8,500,640 B2   8/2013   Nitta et al.
9,610,061 B2   4/2017   Ebbini et al.
(Continued)

FOREIGN PATENT DOCUMENTS

JP   2005-296254 A   10/2005
JP     5219228 B2    6/2013
(Continued)

OTHER PUBLICATIONS

WO 2014181904 translation (Year: 2014).*
(Continued)

*Primary Examiner* — Adil Partap S Virk
(74) *Attorney, Agent, or Firm* — Jefferson IP Law, LLP

(57) ABSTRACT

An electronic device is provided. The electronic device includes a photoplethysmography (PPG) sensor comprising a light source and a light sensor, an ultrasonic device, at least one processor operatively connected to the PPG sensor and the ultrasonic device, and a memory operatively connected with the at least one processor. The memory may store one or more instructions which, when executed, cause the at least one processor to acquire a PPG signal based on light detected by the light sensor, and control the operation of the ultrasonic device on the basis of an index value indicating the quality of the PPG signal.

15 Claims, 18 Drawing Sheets

(52) U.S. Cl.
CPC .......... *A61B 5/7221* (2013.01); *A61B 5/7455* (2013.01); *A61B 5/7475* (2013.01); *A61B 8/02* (2013.01)

(58) Field of Classification Search
CPC ..... A61B 5/7475; A61B 8/4427; A61B 8/461; A61B 2562/0204; A61B 5/0059; A61B 5/0095; A61B 5/021; A61B 5/02108; A61B 5/024; A61B 5/02416; A61B 5/0261; A61B 5/08; A61B 5/0806; A61B 5/0816; A61B 5/6826; A61B 5/7203; A61B 8/4416; A61B 5/00; A61N 7/00
See application file for complete search history.

(56) References Cited

U.S. PATENT DOCUMENTS

| | | | |
|---|---|---|---|
| 10,592,718 B2 | 3/2020 | Khuri-Yakub et al. | |
| 10,691,912 B2 | 6/2020 | Khuri-Yakub et al. | |
| 11,023,704 B2 | 6/2021 | Khuri-Yakub et al. | |
| 11,083,380 B2 | 8/2021 | Kwon et al. | |
| 2006/0206105 A1* | 9/2006 | Chopra | A61N 7/02 607/96 |
| 2008/0312533 A1* | 12/2008 | Balberg | A61B 5/14546 600/437 |
| 2009/0012399 A1 | 1/2009 | Sunagawa et al. | |
| 2010/0113905 A1 | 5/2010 | Park | |
| 2015/0157262 A1* | 6/2015 | Schuessler | A61B 5/0533 600/479 |
| 2015/0283277 A1* | 10/2015 | Schafer | A61L 2/0029 422/128 |
| 2016/0027991 A1* | 1/2016 | Suzuki | H10N 39/00 600/447 |
| 2016/0196635 A1* | 7/2016 | Cho | G06T 3/40 345/660 |
| 2017/0277937 A1* | 9/2017 | Baek | A61B 5/4875 |
| 2017/0296140 A1 | 10/2017 | Ebbini et al. | |
| 2018/0098747 A1* | 4/2018 | Lambert | A61B 8/54 |
| 2019/0133533 A1 | 5/2019 | Alam et al. | |
| 2020/0100705 A1 | 4/2020 | Dellimore et al. | |
| 2020/0117931 A1* | 4/2020 | Nilsson | A61B 5/117 |

FOREIGN PATENT DOCUMENTS

| | | | |
|---|---|---|---|
| JP | 2017-158610 A | 9/2017 | |
| JP | 2019-098049 A | 6/2019 | |
| KR | 10-2010-0048359 A | 5/2010 | |
| KR | 10-1462024 B1 | 11/2014 | |
| KR | 10-2015-0082038 A | 7/2015 | |
| KR | 10-2006035 B1 | 7/2019 | |
| KR | 10-2020-0022135 A | 3/2020 | |
| WO | 2006/082966 A1 | 8/2006 | |
| WO | WO-2014181904 A1 * | 11/2014 | ........... A61B 5/0285 |

OTHER PUBLICATIONS

International Search Report dated Oct. 12, 2021, issued in International Application No. PCT/KR2021/007409.
Korean Office Action dated Mar. 12, 2025, issued in a Korean Patent Application No. 10-2020-0086000.

* cited by examiner

ELECTRONIC DEVICE COMPRISING ULTRASONIC DEVICE AND PPG SIGNAL ACQUISITION METHOD THEREOF

CROSS-REFERENCE TO RELATED APPLICATION(S)

This application is a continuation application, claiming priority under § 365(c), of an International application No. PCT/KR2021/007409, filed on Jun. 14, 2021, which is based on and claims the benefit of a Korean patent application number 10-2020-0086000, filed on Jul. 13, 2020, in the Korean Intellectual Property Office, the disclosure of which is incorporated by reference herein in its entirety.

BACKGROUND

1. Field

The disclosure relates to an electronic device including an ultrasonic device and a photoplethysmography (PPG) signal acquisition method thereof.

2. Description of Related Art

A photoplethysmography (PPG) measurement method is a method of measuring a volume change of a body in an optical manner. In the PPG measurement method, light from a light source is irradiated to a skin, and a difference in a light absorption according to a volume change of a blood vessel in the skin is detected based on an intensity of reflected or transmitting light. A PPG (photoplethysmography) signal is mainly used to monitor a heart rate (HR), respiration, a stress level, a blood pressure (BP), a blood flow rate, and a circulatory system state. Currently, among PPG signal measurement devices, a pulse oximetry is most commonly used. However, the PPG signal may be measured using not only a wrist-type wearable device but also a mobile device such as a smartphone. A PPG sensor of the related art may include one or more light emitters and one or more light receivers. The heart rate (HR) information, heart rate variability (HRV) information may be extracted by detecting peak and valley components of the PPG signal.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic device and a method capable of acquiring a PPG signal of good quality when measuring the PPG signal in a low-temperature environment or measuring the PPG signal of an elderly person, woman, or child with a weak heartbeat, or even when a sensitivity of a light receiver of a PPG sensor is weak due to a configuration of a device.

Additional aspects will be set forth in part in the description which follows and, in part, will be apparent from the description, or may be learned by practice of the presented embodiments.

In accordance with an aspect of the disclosure, an electronic device is provided. The electronic device includes a photoplethysmography (PPG) sensor including a light source and a light detector, an ultrasonic device, at least one processor operatively connected to the PPG sensor and the ultrasonic device, and a memory operatively connected to the at least one processor, wherein the memory may store therein one or more instructions, wherein when the instructions are executed by the at least one processor, the instructions may cause the at least one processor to acquire a PPG signal based on light detected by the light detector, and control an operation of the ultrasonic device based on an indicator value indicating a quality of the PPG signal.

In accordance with another aspect of the disclosure, a PPG signal acquisition method by an electronic device including an ultrasonic is provided. The method includes, based on detecting an object, emitting, by the ultrasonic device, an ultrasonic wave toward the object, based on detecting the object, irradiating, by a light source included in the electronic device, light toward the object, detecting, by a light detector included in the electronic device, light reflected from the object, acquiring a PPG signal based on the detected light, calculating an indicator value indicating a quality of the PPG signal, and controlling an operation of the ultrasonic device based on the indicator value.

According to various embodiments of the disclosure, the ultrasonic waves using the ultrasonic device are emitted, and, at the same time, or thereafter, the PPG (photoplethysmography signal) is measured. Thus, the PPG signal of good quality may be acquired even in an environment where an intensity (magnitude) of a signal component decreases.

Further, according to various embodiments of the disclosure, even when a 2D array imaging sensor is used as a PPG sensor, information requiring high-speed data processing, such as heart rate variability (HRV) may be acquired additionally from the acquired PPG signal.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
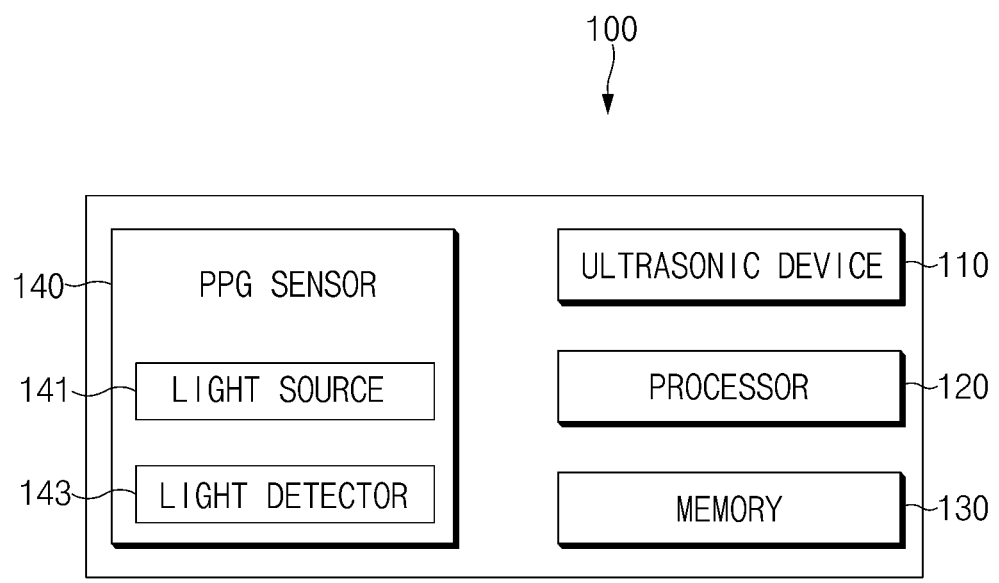
FIG. 1 is a block diagram of an electronic device acquiring a photoplethysmography (PPG) signal according to an embodiment of the disclosure.

FIG. 1 is a block diagram of an electronic device acquiring a photoplethysmography (PPG) signal according to an embodiment of the disclosure.

Referring to FIG. 1, an electronic device 100 according to an embodiment may include an ultrasonic device 110, a processor 120, a memory 130, and a PPG sensor 140.

According to an embodiment of the disclosure, the PPG sensor 140 may include at least one light source 141 and at least one light detector 143. The PPG sensor 140 may irradiate light to an object and detect light reflected from or transmitting through the object. The light detected by the PPG sensor 140 is expressed in a form of light intensity. This is called a PPG signal.

According to an embodiment of the disclosure, the PPG sensor 140 may exist independently in the electronic device 100. However, the disclosure is not limited thereto. According to another embodiment of the disclosure, even when the electronic device 100 does not have a separate light source and a separate light detector for measuring the PPG signal, the PPG signal may be measured using another light source and another light detector included in the electronic device 100. The light source 141 and the light detector 143 of the electronic device 100 used to measure the PPG signal may be collectively referred to as the PPG sensor 140. According to an embodiment of the disclosure, the light source 141 may be a light source of a display panel (e.g., a display panel 230 in FIG. 2). According to an embodiment of the disclosure, the light detector 143 may be at least one image sensor included in the electronic device 100 (e.g., a light sensor of a camera 440 in FIG. 4). The PPG sensor 140 may refer to a module including the light source 141 and the light detector 143 used to measure the PPG signal.

In addition, the PPG signal includes an alternate current (AC) component and a direct current (DC) component, and the AC component may be used to monitor a heart rate, respiration, a stress level, a blood pressure, a blood flow rate, and/or a state of a circulatory system. On the other hand, the DC component may correspond to a noise component. The quality of the PPG signal may be expressed as a ratio AC/DC of the AC component to the DC component, which is referred to as a perfusion index (PI). For example, as the AC component increases, the PI value increases and the quality of the PPG signal improves. In this regard, the improvement in the quality of the PPG signal means that the information (the heart rate, the heart rate variability, the oxygen saturation, the stress level, the blood pressure, the blood flow rate, or the state of the circulatory system) to be acquired based on the PPG signal in a given environment (e.g., an ambient temperature of the electronic device 100, an age and a gender of the user, and a configuration and a structure of the electronic device 100) may be easily acquired.

According to an embodiment of the disclosure, the light source 141 may emit light of at least one wavelength to an outside of the electronic device 100. The light source 141 may include an additional light source for measuring the PPG signal or a light source (e.g., organic light emitting diodes (OLED)) of a display panel (not shown) of the electronic device 100.

According to an embodiment of the disclosure, the light detector 143 may detect light reflected from the object outside the electronic device 100. In this case, the remainder of light emitted from the light source 141 except for a portion of the light absorbed by the object may be reflected from or transmit through the object and thus may become at least a portion of the light detected by the light detector 143. According to an embodiment of the disclosure, the light detector 143 may be a point detector or a two-dimensional (2D) array image sensor. The point detector may be, for example, a photo diode. The 2D array image sensor may be, for example, a camera contact image sensor (CIS), a thin film transistor (TFT) array sensor, or an organic photo diode (PD) array sensor.

According to an embodiment of the disclosure, the ultrasonic device 110 may emit ultrasonic waves to the outside of the electronic device 100. According to an embodiment of the disclosure, the ultrasonic device 110 may be included in a fingerprint recognition sensor (not shown) of the electronic device 100. For example, the ultrasonic device 110 may emit ultrasonic waves toward a touching object when the fingerprint recognition sensor (not shown) detects a touch of the object (e.g., a user's finger). In another embodiment of the disclosure, the ultrasonic device 110 may be integrated with the PPG sensor 140. However, the disclosure is not limited thereto, and according to an embodiment of the disclosure, it may be suffice that the ultrasonic device 110 and the PPG sensor 140 are included in one electronic device.

According to an embodiment of the disclosure, the processor 120 may be operatively connected to the PPG sensor 140 and the ultrasonic device 110. The processor 120 may execute, for example, software (e.g., a program) to control at least one other component (e.g., the light source 141, the light detector 143, the ultrasonic device 110) of the electronic device 100 connected to the processor 120, and to perform various data processing or calculations.

According to an embodiment of the disclosure, in at least a portion of data processing or operation, the processor 120 may load a command or data received from another component (e.g., the light detector 143) into a volatile memory, and may process the command or data stored in the volatile memory, and may store the resulting data in a non-volatile memory.

According to an embodiment of the disclosure, the processor 120 may include a main processor (e.g., a central processing unit or an application processor), and an auxiliary processor (e.g., a graphics processing unit, an image signal processor, a sensor hub processor, or a communication processor) operable independently thereof or together therewith.

According to an embodiment of the disclosure, the processor 120 may control the ultrasonic device 110 to emit ultrasonic waves. According to an embodiment of the disclosure, the processor 120 may control the light source 141 to emit light. According to an embodiment of the disclosure, the processor 120 may control the light detector 143 to detect the light reflected from the object.

According to an embodiment of the disclosure, the processor 120 may control the ultrasonic device 110 to emit ultrasonic waves when the object contacts a touch sensor (e.g., a touch panel) corresponding to the ultrasonic device 110. According to an embodiment of the disclosure, the processor 120 may control the light source to emit light or the light detector to detect light when the object contacts an object recognition area of the PPG sensor 140. The object recognition area of the PPG sensor 140 means an area that detects the contact of the object in order to operate the PPG sensor 140. For example, the object recognition area of the PPG sensor 140 may mean an area in which the touch sensor (e.g., the touch panel) or an image sensor (e.g., a camera) corresponding to the PPG sensor 140 is disposed.

According to an embodiment of the disclosure, the processor 120 may control the ultrasonic device 110 and the PPG sensor 140 to simultaneously operate in response to the contact of the object with the object recognition area of the PPG sensor 140. For example, when the ultrasonic device 110 and the PPG sensor 140 are integrated with each other, or when a spacing between the ultrasonic device 110 and the PPG sensor 140 is within a predefined distance, the processor 120 may control the ultrasonic device 110 and the PPG sensor 140 to simultaneously operate in response to the contact of the object with the object recognition area of the PPG sensor 140.

According to another embodiment of the disclosure, the processor 120 may control the ultrasonic device 110 and the PPG sensor 140 to sequentially operate in response to the contact of the object with the object recognition area of the PPG sensor 140. The processor 120 may control the ultrasonic device 110 and the PPG sensor 140 to sequentially operate by a designated time interval in response to the contact of the object with the object recognition area of the PPG sensor 140. For example, in response to the contact of the object with the object recognition area of the PPG sensor 140, the processor 120 may first operate the ultrasonic device 110 and, after a specified period of time has elapsed, may operate the PPG sensor 140.

According to an embodiment of the disclosure, the processor 120 may acquire the PPG signal from the light detected via the light detector 143. According to an embodiment of the disclosure, the processor 120 may acquire the PPG signal based on an intensity of the light detected via the light detector 143.

According to an embodiment of the disclosure, the processor 120 may determine the quality of the acquired PPG signal. According to an embodiment of the disclosure, the processor 120 may calculate the PI value of the PPG signal. The PI value may be calculated based on a following Equation 1:

$$PI(\text{Perfusion Index}) = \frac{AC}{DC} = \frac{I_H - I_L}{I_L} \qquad \text{Equation 1}$$

In the above Equation 1, AC means the AC component, DC means the DC component, $I_H$ means a maximum intensity of the reflected light, and $I_L$ mean a minimum intensity of the reflected light. The PPG sensor 140 according to an embodiment may irradiate light from the light source 141 to the object to be measured (e.g., the user's skin). At least a portion of the light reaches a blood vessel, and a variable amount according to change in blood flow is absorbed by the blood vessel. The remaining portion of light after the portion being absorbed by the blood vessel may be reflected from or transmit the blood vessel and thus reach the light detector 143. At this time, the PPG signal detected by the light detector 143 may include the AC (alternating current component) corresponding to a portion reflected from an arterial blood which causes the volume change of the blood vessel due to the heartbeat, and then reaching the light detector 143, and the DC (direct current) component corresponding to a portion reflected from an area other than the arterial blood and then reaching the light detector 143. The PI (Perfusion Index) value as one of an indicator value indicating the signal quality of the PPG sensor may be the ratio of the AC and DC components included in the PPG signal (PI=AC/DC.)

According to an embodiment of the disclosure, when an indicator value (e.g., the PI value) indicating the quality of the PPG signal is determined to be greater than or equal to a threshold value, the processor 120 may extract at least one of heart rate information, respiration information, stress information, and blood pressure information, or blood flow amount information, based on the acquired PPG signal. In general, for human skin, the PI value of the PPG signal may be around 1%, and therefore, according to an embodiment of the disclosure, the threshold value of the quality of the PPG signal may be 1% as the PI value. In the embodiment of the disclosure as described with reference to FIG. 1, an example in which the PI value acts as the indicator value indicating the quality of the PPG signal has been described. However, the disclosure is not limited thereto and other indicator values indicating the quality of the PPG signal may be used.

According to an embodiment of the disclosure, the processor 120 may control an operation of the ultrasonic device 110 based on the indicator value indicating the quality of the PPG signal. According to an embodiment of the disclosure, when it is determined that the indicator value is greater than or equal to the threshold value, the processor 120 may control the ultrasonic device 110 not to emit ultrasonic waves. According to an embodiment of the disclosure, when it is determined that the indicator value is smaller than the threshold value, the processor 120 may control the ultrasonic device 110 to emit ultrasonic waves.

According to an embodiment of the disclosure, when it is determined that the indicator value indicating the quality of the PPG signal is smaller than the threshold value, the processor 120 may adjust at least one of a power level or an emission time duration of the ultrasonic wave emitted from the ultrasonic device 110.

Human arterial blood may be distributed in a first plexus distributed between the epidermis layer and the dermis layer and in a second plexus distributed between the dermis layer and the hypodermis layer. A thickness of the epidermis layer of human skin is usually 0.5 mm, and a thickness of the dermis layer is usually 1 to 1.5 mm. According to an embodiment of the disclosure, the light source 141 may emit light of an intensity adjusted such that that the light can reach the first plexus.

According to an embodiment of the disclosure, when the intensity of the PPG signal based on the light detected by the light detector 143 is greatly attenuated, the processor 120 increases an intensity of the light emitted from the light source 141 to compensate for loss in the light detector 143. However, the increased intensity of the light may be greater than an intensity level safe for irradiation to human skin.

Further, the human blood vessel contracts or expands to maintain a body temperature according to temperature change in an ambient environment. For example, in a low-temperature environment, the blood vessel contracts to minimize heat loss through the blood vessel. This reduces the AC component of the PPG signal, thus making it difficult to distinguish the AC component from a noise component (e.g., the DC component). Further, the AC component of the PPG signal may decrease even when an intensity of the heartbeat is weak in women, children, and the elderly.

Further, when the PPG sensor is embedded in a mobile device, the AC component after interacting with the blood vessel may decrease while penetrating parts of the mobile device. In another example, when the light sensor of the camera of the mobile device is used as the PPG sensor, a size of a pixel and a signal sensitivity of each pixel may be reduced due to the characteristics of the 2D array of the camera, and summation of pixel information of an entire 2D array may be required to acquire the PPG signal. Thus, it may be difficult to achieve rapid signal acquisition. According to an embodiment of the disclosure, a speed at which the PPG signal is acquired may be limited to a value equal to or smaller than 30 FPS (frame per second). 30 FPS may be, for example, a video imaging speed of a camera.

For the above reasons, it may be difficult to extract information (e.g., HR (heart rate), HRV (heart rate variability), $SpO_2$ (saturation of percutaneous oxygen), a stress level, a blood pressure, a blood flow rate, or a state of a circulatory system) that requires acquisition of a signal of 100 Hz or higher from the PPG signal using light having a safe intensity level which can be irradiated to the skin.

The electronic device 100 according to the disclosure may acquire the PPG signal of improved quality by expanding the user's blood vessel using the ultrasonic device 110 that emits ultrasonic waves while using light of a safe intensity level which can be irradiated to the skin.

According to an embodiment of the disclosure, when the quality of the PPG signal is determined to be smaller than the threshold value, the processor 120 may control whether to emit ultrasonic waves via the ultrasonic device 110 or at least one of an emission time duration or a power level of the ultrasonic waves emitted via the ultrasonic device 110. In the PPG sensor 140 having a reflective structure, the PI value of the PPG signal for human skin may be around 1%. The reflective structure may refer to a structure of the PPG sensor 140 designed so that light emitted from the light source 141 reaches the human skin and is reflected therefrom and then is detected by the light detector 143. According to an embodiment of the disclosure, when it is determined that the PI value indicating the quality of the PPG signal is smaller than 1%, the processor 120 may control whether to emit ultrasonic waves via the ultrasonic device 110. Alternatively, when the processor 120 determines that the PI value indicating the quality of the PPG signal is smaller than 1%, the processor 120 may adjust the power level of the ultrasonic wave emitted through the ultrasonic device 110, or may control the emission time duration of the ultrasonic wave, or may control both the power level of the ultrasonic wave and the emission time duration thereof.

Hereinafter, a case in which the processor 120 controls the power level of an ultrasonic wave emitted from the ultrasonic device 110, based on the indicator value indicating the quality of the PPG signal will be described later.

According to an embodiment of the disclosure, when the indicator value indicating the quality of the PPG signal is determined to be a first value, the processor 120 may control the ultrasonic device 110 to emit ultrasonic waves having a first ultrasonic wave power level. According to an embodiment of the disclosure, when the processor 120 determines that the quality of the PPG signal is a second value, the processor 120 may control the ultrasonic device 110 to emit an ultrasonic wave having a second ultrasonic wave power level. According to an embodiment of the disclosure, each of the first value and the second value may be the PI value, and the second value may be set to be lower than the first value. In this regard, the second ultrasonic wave power level corresponding to the second value may be set to be greater than the first ultrasonic wave power level corresponding to the first value.

Hereinafter, a case in which the processor 120 controls a time duration (emission time duration) for which the ultrasonic device 110 emits ultrasonic waves, based on the indicator value indicating the quality of the PPG signal will be described later.

According to an embodiment of the disclosure, when the indicator value indicating the quality of the PPG signal is determined to be the first value, the processor 120 may control the ultrasonic device 110 to emit ultrasonic waves for a first time duration. According to an embodiment of the disclosure, upon determining that the quality of the PPG signal is the second value, the processor 120 may control the ultrasonic device 110 to emit ultrasonic waves for a second time duration. According to an embodiment of the disclosure, each of the first value and the second value may be the PI value, and the second value may be set to be lower than the first value. In this case, the second time duration corresponding to the second value may be set to be larger than the first time duration corresponding to the first value.

According to an embodiment of the disclosure, the memory 130 may be operatively coupled with at least one processor. The memory 130 may store therein various data used by at least one component (e.g., the processor 120 or the light detector 143) of the electronic device 100. The data may include, for example, software (e.g., a program) and input data or output data related to a command related thereto. The memory 130 may include a volatile memory or a non-volatile memory.

Hereinafter, referring to FIG. 2, a configuration and an operation of an electronic device according to an embodiment of the disclosure will be described.

Figure 2:
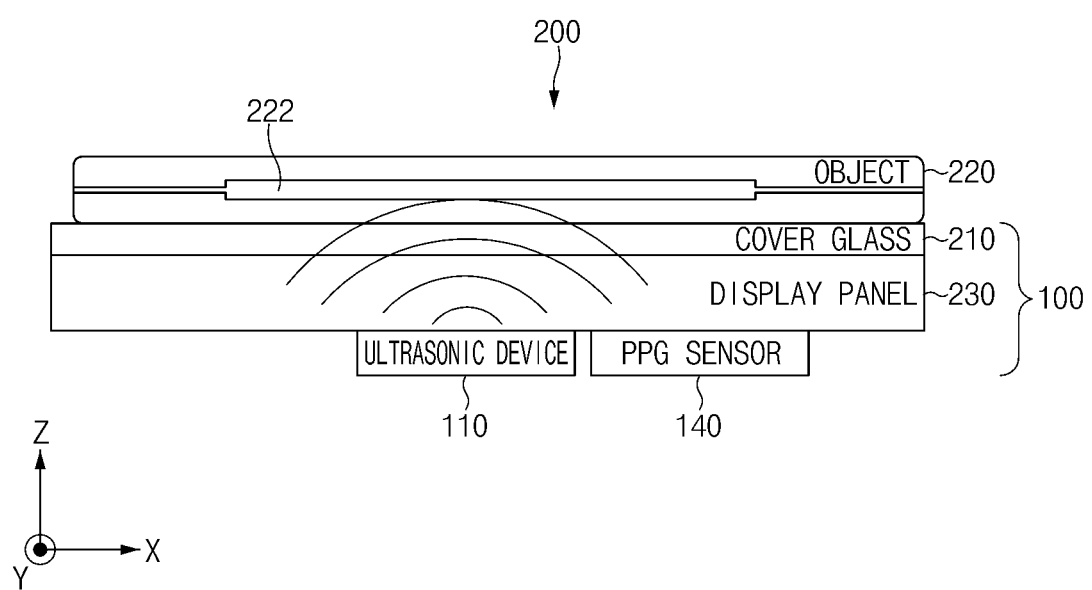
FIG. 2 is a diagram illustrating an electronic device emits ultrasonic waves to expand a blood vessel of an object according to an embodiment of the disclosure.

FIG. 2 is a diagram 200 illustrating an electronic device emits ultrasonic waves to expand a blood vessel of an object according to an embodiment of the disclosure. According to an embodiment of the disclosure, the electronic device 100 referring to FIG. 2 may be the same as the electronic device 100 as shown in FIG. 1. Therefore, although a component (e.g., the processor 120 or the memory 130 in FIG. 1) is not shown in FIG. 2, it is assumed that the electronic device 100 as shown in FIG. 2 includes the component included in the electronic device 100 as shown in FIG. 1. According to an embodiment of the disclosure, the electronic device 100 may be a smart phone, a tablet PC, or a smart watch. However, the disclosure is not limited thereto.

Referring to FIG. 2, the electronic device 100 according to an embodiment may further include the display panel 230 and a cover glass 210. According to an embodiment of the disclosure, the display panel 230 and the cover glass 210 may be stacked in a Z-axis direction. The cover glass 210 may be a member to protect the components of the electronic device 100 including the display panel 230 from an outside, and may be disposed on a front face (or a top face) of the display panel 230.

According to an embodiment of the disclosure, the cover glass 210 may be embodied as a polymer base film (e.g., made of polyimide, polyarylate, poly ethylene terephthalate, polyethersulphone, polyethylene naphthalate, or polyacrylate, polycarbonate), or a glass film.

Referring to FIG. 2, according to an embodiment of the disclosure, the ultrasonic device 110 and the PPG sensor 140 may be disposed on a rear face (or a bottom face) of the display panel 230. In FIG. 2, the front face (the top face) of the display panel 230 faces in a positive direction of the Z axis, and the rear face (the bottom face) of the display panel 230 faces in a negative direction of the Z axis.

According to an embodiment of the disclosure, an adhesive member (e.g., a double-sided tape, an adhesive), an elastic member (e.g., silicone or rubber), and/or a liquid material (e.g., gel) may be disposed between the ultrasonic device 110 and the rear face (the bottom face) of the display panel 230.

Figure 16:
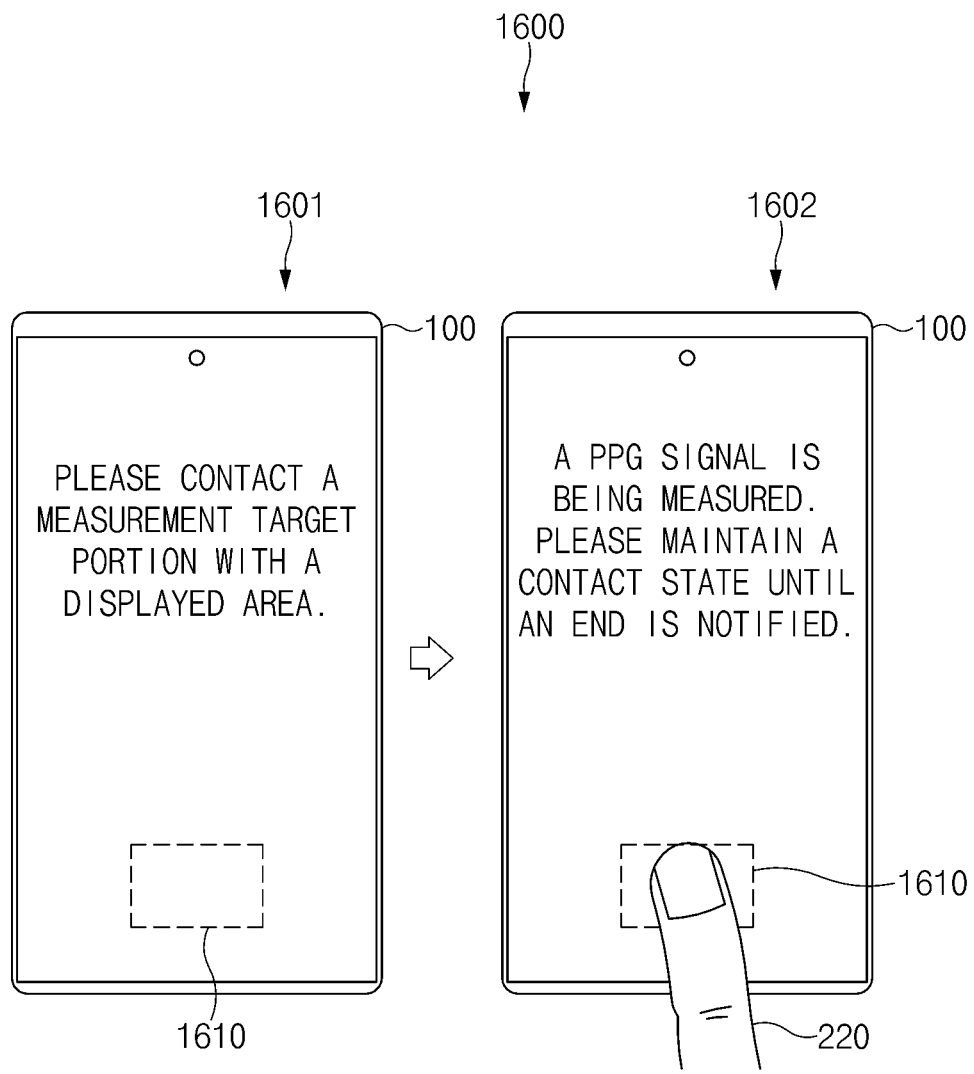
FIG. 16 is a diagram illustrating a user interface provided by an electronic device to acquire a PPG signal according to an embodiment of the disclosure.

Referring to FIG. 2, the electronic device 100 may emit ultrasonic waves using the ultrasonic device 110 to the object recognition area of the PPG sensor 140 (e.g., a first area 1610 in FIG. 16). According to an embodiment of the disclosure, the object recognition area may be displayed as a user interface on a display.

According to an embodiment of the disclosure, an object 220 may be a user's skin. According to an embodiment of the disclosure, the object 220 may be a user's finger. However, the disclosure is not limited thereto.

Referring to FIG. 2, as the ultrasonic device 110 of the electronic device 100 emits ultrasonic waves to the object 220 in contact with the object recognition area of the PPG sensor 140, a blood vessel 222 inside the object 220 may expand. According to an embodiment of the disclosure, the ultrasonic waves emitted from the ultrasonic device 110 may apply mechanical shear stress to endothelial cells of the blood vessel 222 to open a calcium-activated potassium channel in a wall of the blood vessel 222. Nitric oxide is introduced into the blood vessel through the open channel, and the nitric oxide inhibits an action of a vascular smooth muscle contributing to contraction of the blood vessel 222, so that the blood vessel 222 may expand. When the blood vessel 222 expands under this process, the power level of the signal component (AC component) of the PPG signal increases. Thus, even when the noise component (DC component) is not reduced, the PI value corresponding to a SNR (signal to noise ratio) (one of the indicator values indicating the quality of the PPG signal) may be increased.

According to an embodiment of the disclosure, when emission of the ultrasonic waves is stopped after the blood vessel 222 is exposed to the ultrasonic waves, the expanded state of the blood vessel 222 may last for a predefined time duration. According to an embodiment of the disclosure, the electronic device 100 may determine at least one of an emission power level, an emission frequency, or a position of an emission target object of the ultrasonic wave based on a minimum exposure time to the ultrasonic wave for expanding the blood vessel 222 and a time duration for which the expanded state of the blood vessel 222 is maintained by the ultrasonic wave.

According to an embodiment of the disclosure, the power level of the ultrasonic wave emitted from the ultrasonic device 110 of the electronic device 100 may correspond to a power level that changes an ion channel by a mechanical stress of the ultrasonic wave transmitted to the wall of the blood vessel 222.

According to an embodiment of the disclosure, the power level of the ultrasonic wave emitted from the ultrasonic device 110 of the electronic device 100 may be lower than a power level which may cause tissue deformation due to a thermal effect, a cavitation effect, or a mechanical effect of a skin cell such as HIFU (high power level focused ultrasound) treatment. According to an embodiment of the disclosure, the power level of the ultrasonic wave may be in a range of 0.1 to 2 W/cm$^2$.

For example, according to the electronic device 100 according to an embodiment disclosed in the disclosure, a sudden temperature rise of the user's skin or a change in skin tissue is not caused, such that a magnitude of the signal component (AC component) may be amplified while informational characteristics of the PPG signal may be maintained. According to an embodiment of the disclosure, the power level of the ultrasonic wave emitted from the ultrasonic device 110 of the electronic device 100 may be a power level of an ultrasonic wave used in the fingerprint recognition sensor (not shown) of the electronic device 100. However, the disclosure is not limited thereto.

Referring to FIG. 2, the PPG sensor 140 may be included in the electronic device 100 in a separate manner from the ultrasonic device 110. In this case, the PPG sensor 140 may include the light source (e.g., the light source 141 of FIG. 1) and the light detector (e.g., the light detector 143 of FIG. 1).

According to an embodiment of the disclosure, the PPG sensor 140 may operate concurrently or sequentially with an operation of the ultrasonic device 110. According to an embodiment of the disclosure, the PPG sensor 140 may emit light to the object recognition area using the light source. According to an embodiment of the disclosure, the PPG sensor 140 may use the light detector to detect light reflected from the object 220 whose the blood vessel 222 has been expanded by the ultrasonic waves.

Therefore, the electronic device 100 according to an embodiment acquires the PPG signal based on the light reflected from the object 220 whose the blood vessel 222 has been expanded. Thus, the PPG signal with improved quality (in which the noise component is constant but the signal component is increased) may be acquired.

Hereinafter, referring to FIG. 3, a configuration and an operation of an electronic device according to an embodiment of the disclosure will be described.

Figure 3:
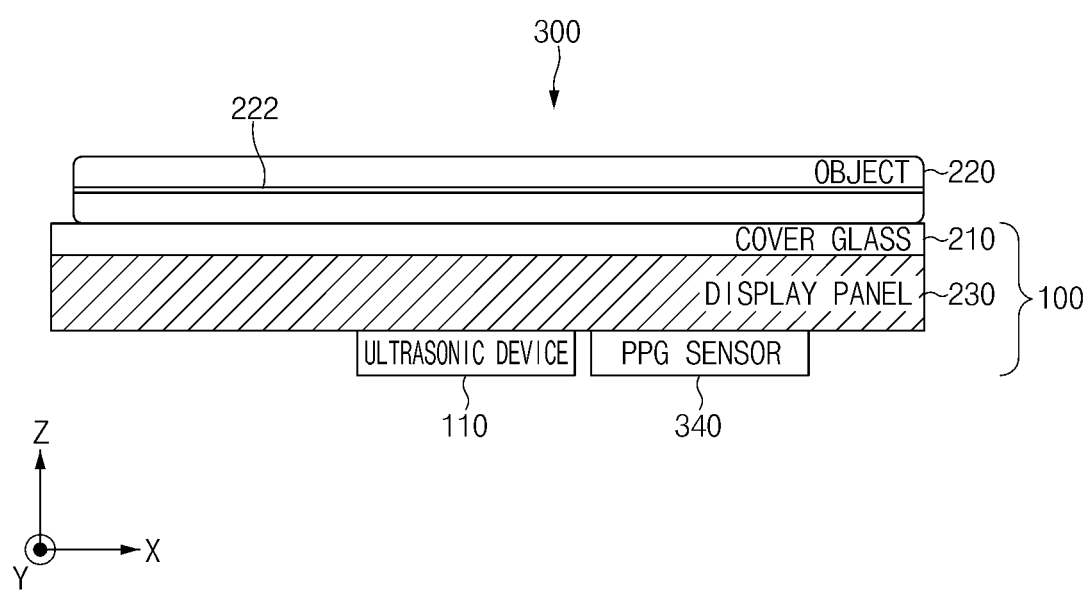
FIG. 3 is a diagram illustrating a configuration of an electronic device according to an embodiment of the disclosure.

FIG. 3 is a diagram 300 illustrating a configuration of an electronic device according to an embodiment of the disclosure. According to an embodiment of the disclosure, the electronic device 100 as shown in FIG. 3 may be the electronic device 100 as shown in FIG. 1. Therefore, although a component (e.g., the processor 120 or the memory 130 in FIG. 1) is not shown in FIG. 3, it is assumed that the electronic device 100 as shown in FIG. 3 includes the component included in the electronic device 100 as shown in FIG. 1. According to an embodiment of the disclosure, the electronic device 100 may be a smart phone, a tablet PC, or a smart watch. However, the disclosure is not limited thereto.

Referring to FIG. 3, the electronic device 100 according to an embodiment may further include the display panel 230 and the cover glass 210. According to an embodiment of the disclosure, the display panel 230 and the cover glass 210 may be stacked in a Z-axis direction. The cover glass 210 may be disposed on the front face (or the top face) of the display panel 230. According to an embodiment of the disclosure, the ultrasonic device 110 and the PPG sensor 140 may be disposed on the rear face (or the bottom face) of the display panel 230. In FIG. 3, the front face (the top face) of the display panel 230 faces in a positive direction of the Z axis, and the rear face (the bottom face) of the display panel 230 faces in a negative direction of the Z axis.

According to an embodiment of the disclosure, a PPG sensor 340 may include the light detector (e.g., the light detector 143 of FIG. 1). According to an embodiment of the disclosure, the PPG sensor 340 may use the light source included in the display panel 230 as a light source for acquiring the PPG signal. The light source included in the display panel 230 may be, for example, a back light unit (BLU) of a light crystal display (LCD), a light emitting diode (LED), a micro LED, or organic light emitting diode (OLED). However, the disclosure is not limited thereto.

According to an embodiment of the disclosure, the light detector may be embodied as an optical sensor operating in a point detector mode, such as a photo diode (PD), an ambient light sensor (ALS), a proximity sensor, or an optical fingerprint sensor, or as an optical sensor operating in a 2D array detector mode such as a CMOS (complementary metal-oxide semiconductor) image sensor (CIS), or a CCD (charge coupled device) image sensor. According to an embodiment of the disclosure, when the PPG sensor 340 operates in the point detector mode, the PPG sensor may operate at 100 Hz or higher of a readout speed. Thus, the electronic device 100 may implement both a HRM (heart rate monitoring) function and a HRV (heart rate variability) function. When the PPG sensor 340 operates in the 2D array detector mode, the PPG sensor may operate at the readout speed lower than 100 Hz. Thus, the electronic device 100 cannot implement, for example, the HRV function. According to various embodiments disclosed in the disclosure, the electronic device may increase the power level of the signal component of the PPG signal by emitting the ultrasonic waves using the ultrasonic device 110. Thus, when the PPG sensor 340 operates in the 2D array detector mode, that is, when the CIS or CCD image sensor is used as the PPG sensor 340, the electronic device 100 may implement both the HRM and HRV functions.

In the embodiment as described above with reference to FIG. 3, an example in which the PPG sensor 340 measures the PPG signal using the light source of the display panel 230 is described. However, according to another embodiment of the disclosure, the PPG sensor may include an own light source.

Hereinafter, referring to FIG. 4, a configuration and an operation of an electronic device according to another embodiment of the disclosure will be described.

Figure 4:
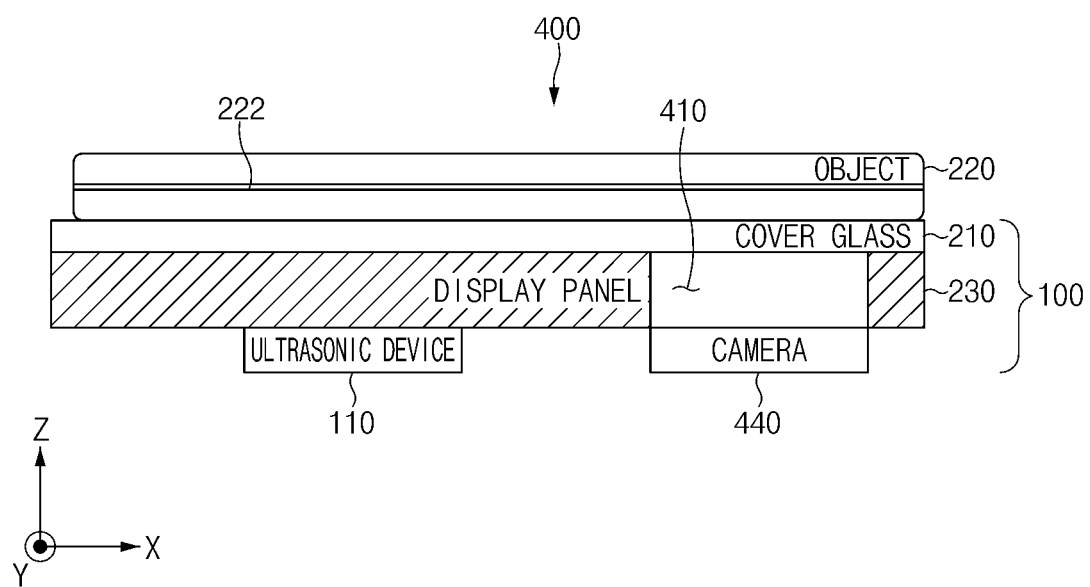
FIG. 4 is a diagram illustrating a configuration of an electronic device according to an embodiment of the disclosure.

FIG. 4 is a diagram 400 illustrating a configuration of an electronic device according to an embodiment. According to an embodiment of the disclosure, the electronic device 100 as shown in FIG. 4 may be the electronic device 100 as shown in FIG. 1. Therefore, although a component (e.g., the processor 120 or the memory 130 in FIG. 1) is not shown in FIG. 4, it is assumed that the electronic device 100 as shown in FIG. 4 includes the component included in the electronic device 100 as shown in FIG. 1. According to an embodiment of the disclosure, the electronic device 100 may be a smart phone, a tablet PC, or a smart watch. However, the disclosure is not limited thereto.

Referring to FIG. 3, the electronic device 100 according to an embodiment may further include the display panel 230, the cover glass 210 and the camera 440. According to an embodiment of the disclosure, the display panel 230 and the cover glass 210 may be stacked in a Z-axis direction. The cover glass 210 may be disposed on the front face (or the top face) of the display panel 230.

Referring to FIG. 4, the ultrasonic device 110 may be disposed on the rear face (or the bottom face) of the display panel 230. In FIG. 4, the front face (the top face) of the display panel 230 faces in a positive direction of the Z axis, and the rear face (the bottom face) of the display panel 230 faces in a negative direction of the Z axis.

Referring to FIG. 4, the camera 440 is disposed on the rear face (or the bottom face) of the display panel 230, and may be disposed at a position corresponding to a hole 410 extending through the front and rear faces of the display panel 230. Accordingly, according to an embodiment of the disclosure, the hole 410 may be a hole for exposing a camera lens.

According to an embodiment of the disclosure, the electronic device 100 may use the light source (e.g., OLED) of the display panel 230 as the light source of the PPG sensor (e.g., the PPG sensor 140 in FIG. 1). The electronic device 100 according to an embodiment may emit light using the light source of the display panel 230 to acquire the PPG signal.

According to an embodiment of the disclosure, the electronic device 100 may use a light sensor (e.g., a CMOS image sensor) included in the camera 440 as the light detector of the PPG sensor. The electronic device 100 according to an embodiment may detect light reflected from the object 220 using the camera 440 to acquire the PPG signal.

In the embodiment as described above with reference to FIG. 4, an example in which the PPG signal is acquired using the light sensor of the camera 440 is described. However, the disclosure is not limited thereto. A 2D array image sensor included in the electronic device 100 may be used to detect reflected or transmitting the light from or through the object 220.

According to an embodiment of the disclosure, when the electronic device 100 uses a two-dimensional array image sensor, the electronic device 100 may implement the HRM (heart rate monitoring) function with a data readout speed based on the two-dimensional array pixel but may not implement the HRV (heart rate variability) function requiring high-speed measurement.

A CIS pixel or a CCD pixel of a 2D array is small in size and thus has poor sensitivity. For this reason, to acquire the PPG signal, a scheme of summing information from all of 2D array pixels is used. Therefore, a data readout speed may be limited to a readout speed of an entire frame. For example, the electronic device 100 may control the ultrasonic device 110 to emit ultrasonic waves to expand the blood vessel 222 of the object 220 to amplify the signal component of the PPG signal. Therefore, the electronic device 100 may acquire the PPG signal by summing pixel values of at least one row without summing all pixel values of the two-dimensional array. For example, the electronic device 100 as shown in FIG. 4 expands the blood vessel 222 of the object 220 using the ultrasonic device 110. Thus, even when the electronic device 100 does not include a separate PPG sensor, the electronic device 100 as shown in FIG. 4 may acquire the PPG signal using the light source of the display panel 230 and the 2-dimensional array image sensor (e.g., the camera 440) included in the electronic device 100. Then, based on the acquired PPG signal, the electronic device 100 may implement only the HRM function, but also the HRV function.

For example, since the display panel 230 does not exist between the blood vessel 222 of the object 220 and the camera 440, light transmittance attenuation due to the display panel 230 may not occur.

In the embodiment with reference to FIG. 4, an example where the camera 440 is a front camera of the electronic device 100 and the electronic device measures the PPG signal using the front camera 440 and the light source of the display panel 230 is described. However, the disclosure is not limited thereto. In another example, the electronic device 100 may measure the PPG signal using a rear camera of the electronic device and a flash light source of the rear camera.

Hereinafter, with reference to FIG. 5, an operation in which an electronic device according to an embodiment acquires a PPG signal will be described.

Figure 5:
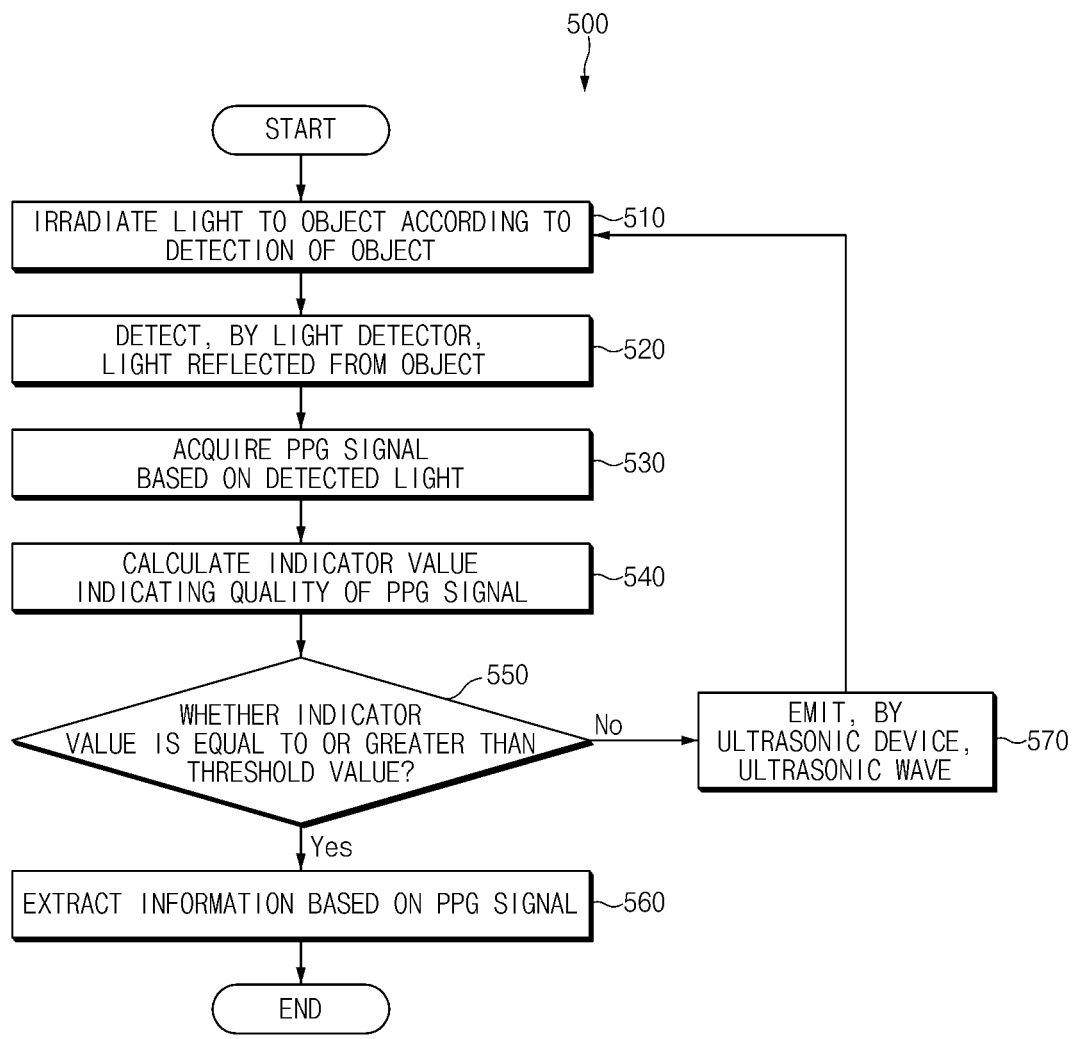
FIG. 5 is a flowchart illustrating a method in which an electronic device acquires a PPG signal according to an embodiment of the disclosure.

FIG. 5 is a flow chart 500 illustrating a method in which an electronic device acquires a PPG signal according to an embodiment of the disclosure. Hereinafter, an operation of the electronic device as described with reference to FIG. 5 may be an operation of the electronic device 100 in FIG. 1, and may be performed by the processor (e.g., the processor 120 in FIG. 1) of the electronic device.

Referring to FIG. 5, in operation 510, according to an embodiment of the disclosure, the electronic device may detect the object contacting the object recognition area of the PPG sensor (e.g., the PPG sensor 140 in FIG. 1). According to an embodiment of the disclosure, the object recognition area of the PPG sensor (e.g., the first area 1610 in FIG. 16) may be the same as an area of the object detected by a touch sensor (e.g., a touch panel) corresponding to the ultrasonic device (e.g., the ultrasonic device 110 in FIG. 1). In another example, the object recognition area of the PPG sensor (e.g., a second area 1720 in FIG. 17) may be different from an area (e.g., a first area 1710 in FIG. 17) of the object detected by a touch sensor (e.g., a touch panel) corresponding to the ultrasonic device.

In operation 520, according to an embodiment of the disclosure, as the object is detected, the electronic device may operate the light source (e.g., light source 141 of FIG. 1) of the PPG sensor to emit light. According to an embodiment of the disclosure, the light source of the PPG sensor radiates light so that the light may be radiated to the object in contact with the object recognition area of the PPG sensor. At this time, at least a portion of the light reaching the object may be absorbed by the object, and the rest thereof may be reflected from or transmit through the object.

According to an embodiment of the disclosure, when the ultrasonic device and the PPG sensor are integrated with each other or are spaced from each other by a spacing equal to or smaller than a predefined distance, the electronic device may operate the ultrasonic device and the PPG sensor in response to one time detection of the object. According to an embodiment of the disclosure, in response to one time detection of the object, the electronic device may simultaneously operate the ultrasonic device and the PPG sensor or sequentially operate the ultrasonic device and the PPG sensor by a designated interval.

In another embodiment of the disclosure, when the ultrasonic device and the PPG sensor are spaced apart from each other by a spacing larger than or equal to a predefined distance, the electronic device may perform an object detection operation using the touch sensor (e.g., the touch panel) corresponding to the ultrasonic device before operating the PPG sensor. Then, when the touch sensor has detected the object, the electronic device may use the ultrasonic device to emit the ultrasonic waves. For example, an area of the object detected by the touch sensor may be an area different from the object recognition area of the PPG sensor.

According to an embodiment of the disclosure, when the ultrasonic device and the PPG sensor are spaced apart from each other by a spacing larger than or equal to the predefined distance, the predefined distance may be smaller or equal to 3 cm.

In operation 520, according to an embodiment of the disclosure, the electronic device may operate the light detector (e.g., the light detector 143 of FIG. 1) of the PPG sensor to detect the light reflected from the object. Operation 520 may be performed concurrently with operation 510.

In operation 530, according to an embodiment of the disclosure, the electronic device may acquire the PPG signal based on the detected light. According to an embodiment of the disclosure, the PPG signal may be based on the intensity of the light detected by the light detector. The PPG signal may include the AC component as the signal component capable of extracting various information reflecting the characteristics of the circulatory system, and the DC component corresponding to the noise component in relation to the signal component.

In operation 540, according to an embodiment of the disclosure, the electronic device may calculate the indicator value indicating the quality of the PPG signal. According to an embodiment of the disclosure, the electronic device may calculate the PI value corresponding to the ratio of the AC component and the DC component of the PPG signal. According to an embodiment of the disclosure, the electronic device may determine whether the PI value of the PPG signal is greater than or equal to the threshold value and determine the quality of the PPG signal based on the determination result in operation 550. According to an embodiment of the disclosure, the threshold value may be 'PI value 1%'.

In operation 550, when the electronic device according to an embodiment determines that the indicator value indicating the quality of the PPG signal is greater than or equal to the threshold value, the electronic device may perform operation 560 of extracting information based on the PPG signal. According to an embodiment of the disclosure, operation 560 may be an operation in which the electronic device extracts information about at least one of the heart rate, the respiration, the stress level, the blood pressure, and the blood flow rate, based on the AC component of the PPG signal. According to an embodiment of the disclosure, the extracted information may be information for monitoring the state of the circulatory system.

In operation 550, when the electronic device according to an embodiment determines that the indicator value (e.g., the PI value) indicating the quality of the PPG signal is smaller than the threshold value, the electronic device may control the ultrasonic device (e.g., the ultrasonic device 110 in FIG. 1) to emit the ultrasonic waves in operation 570.

In operation 570, according to an embodiment of the disclosure, the electronic device may detect the object contacting the object recognition area (e.g., the first area 1610 of FIG. 16) of the ultrasonic device using the touch sensor (e.g., the touch panel). According to an embodiment of the disclosure, the object recognition area of the ultrasonic device may be a fingerprint recognition area.

According to an embodiment of the disclosure, when the electronic device includes the display panel (e.g., the display panel 230 in FIG. 2), and the ultrasonic device is disposed on the bottom face of the display panel, the electronic device may detect the contact of the object at a position on the display corresponding to the ultrasonic device. According to an embodiment of the disclosure, the electronic device may detect the contact of the object via the touch sensor or a pressure sensor.

In operation 570, as the object has been detected, the electronic device according to an embodiment may operate the ultrasonic device to emit ultrasonic waves. According to an embodiment of the disclosure, as the ultrasonic device of the electronic device emits the ultrasonic waves, the object in contact with the object recognition area of the ultrasonic device may be exposed to the ultrasonic waves. According to an embodiment of the disclosure, the electronic device may emit the ultrasonic waves at a preset power level and for a preset time duration. According to an embodiment of the disclosure, the ultrasonic wave emitted from the electronic device may expand a blood vessel (e.g., the blood vessel 222 of FIG. 4) inside the object.

According to an embodiment of the disclosure, as it is determined that the indicator value indicating the quality of the PPG signal is smaller than the threshold value in operation 550, the electronic device may perform an operation (not shown) of increasing the power level of the ultrasonic wave emitted from the ultrasonic device. For example, it may be assumed that the power level of the emitted ultrasonic wave before increasing the power level of the ultrasonic wave is a first power level. As the indicator value is determined to be smaller than the threshold value, the electronic device according to an embodiment may adjust the power level of the ultrasonic wave emitted from the ultrasonic device from the first power level to a second power level. In this regard, the second power level may mean a power level relatively greater than the first power level. After increasing the power level of the ultrasonic wave emitted from the ultrasonic device, the electronic device according to an embodiment may perform operation 510 to operation 560 again.

According to an embodiment of the disclosure, when the electronic device determines that the indicator value (e.g., the PI value) indicating the quality of the PPG signal is a first value in operation 550, the electronic device may adjust the power level of the ultrasonic wave emitted from the ultrasonic device to a first power level. When the electronic device determines that the indicator value (e.g., the PI value) indicating the quality of the PPG signal is a second value in operation 550, the electronic device may adjust the power level of the ultrasonic wave emitted from the ultrasonic device to a second power level. In this regard, the second value (e.g., 0.5%) may be smaller than the first value (e.g., 1%), and the second ultrasonic wave power level may be greater than the first ultrasonic wave power level.

According to another embodiment of the disclosure, as it is determined in operation 550 that the indicator value indicating the quality of the PPG signal is smaller than the threshold value, the electronic device may perform an operation (not shown) of increasing the emission time duration of the ultrasonic waves. For example, it may be assumed that an ultrasonic wave emission time duration before increasing the ultrasonic wave emission time duration is a first time duration. As it is determined that the indicator value is smaller than the threshold value in operation 550, the electronic device according to an embodiment may adjust the time duration for which the ultrasonic device emits the ultrasonic waves to a second time duration. In this case, the second time duration may mean a relatively larger time than the first time duration. After increasing the time duration for which the ultrasonic device emits the ultrasonic waves, the electronic device according to an embodiment may perform operation 510 to operation 560 again.

According to an embodiment of the disclosure, when the electronic device determines that the indicator value (e.g., the PI value) indicating the quality of the PPG signal is a first value in operation 550, the electronic device may control the ultrasonic device to emit the ultrasonic waves during a first time duration. When the electronic device determines that the indicator value (e.g., the PI value) indicating the quality of the PPG signal is a second value in operation 550, the electronic device may control the ultrasonic device to emit the ultrasonic waves during a second time duration. In this regard, the second value (e.g., 0.5%) may be smaller than the first value (e.g., 1%), and the second time duration may be larger than the first time duration.

Hereinafter, with reference to FIGS. 6 and 7, an arrangement structure of components of an electronic device not including an ultrasonic device, and a state of the blood vessel 222 when the electronic device acquires a PPG signal will be described.

Figure 6:
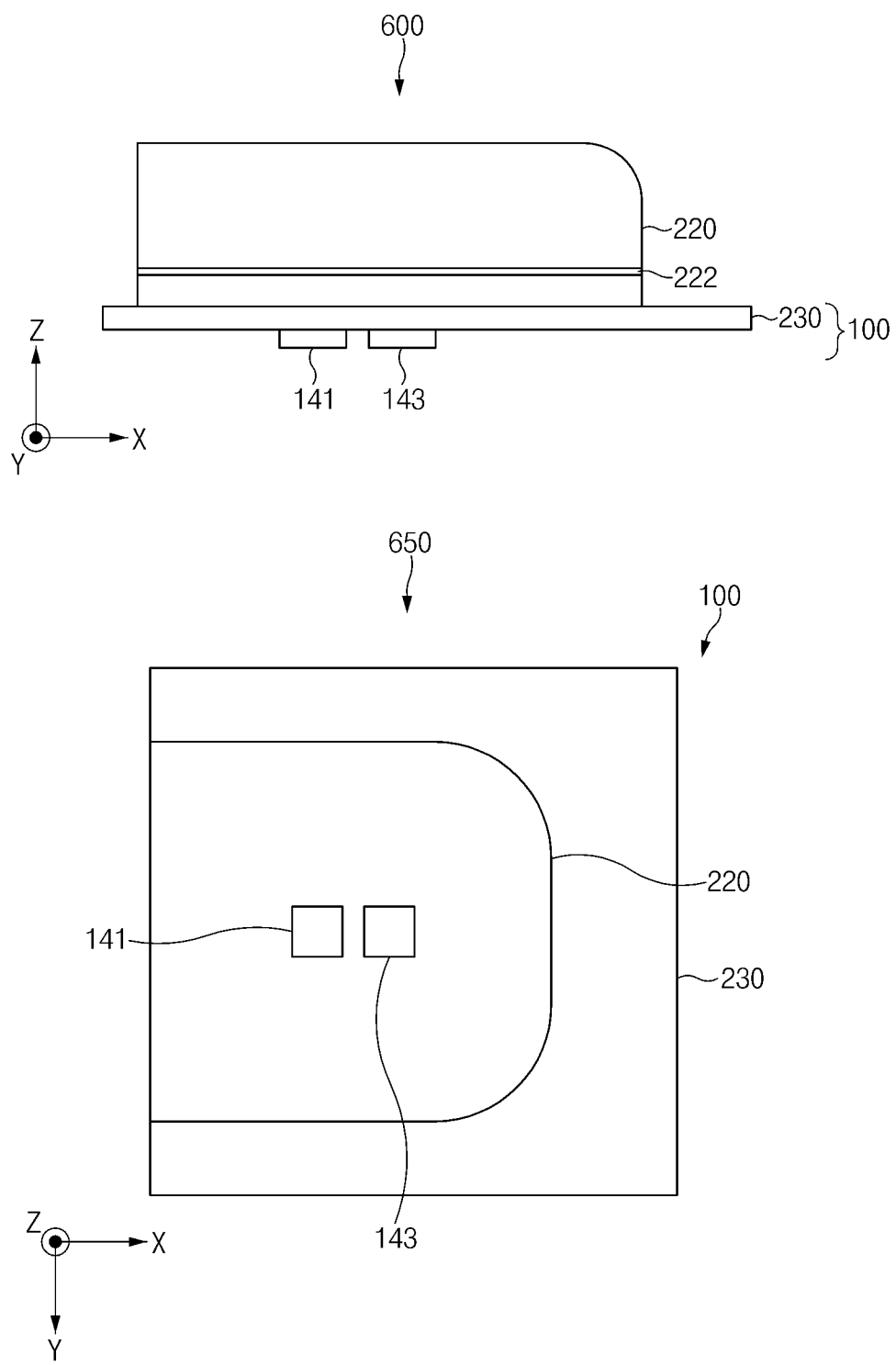
FIG. 6 is a diagram illustrating an electronic device not including an ultrasonic device acquires a PPG signal from an object according to an embodiment of the disclosure.

FIG. 6 is diagrams 600 and 650 illustrating an electronic device not including an ultrasonic device acquires a PPG signal from an object according to an embodiment of the disclosure.

Referring to FIG. 6, it illustrates a PPG signal acquisition electronic device of the related art acquires the PPG signal from the object. FIG. 6 includes the side cross-sectional view 600 and the projection plan view 650 showing that the electronic device 100 acquires the PPG signal from the object 220.

Referring to FIG. 6, in the electronic device 100, the light source 141 and the light detector 143 may be arranged side by side and may be disposed on the bottom face of the display panel 230. In this regard, a distance between the light source 141 and the light detector 143 may be adjusted based on a depth by which light is to be transmitted to an inside of the object (e.g., the user's skin). According to an embodiment of the disclosure, the light source 141 may be an independent light source for acquiring the PPG signal. Since the electronic device 100 in FIG. 6 does not include the ultrasonic device (e.g., the ultrasonic device 110 in FIG. 1), blood vessel expansion by the ultrasonic waves does not occur.

Figure 7:
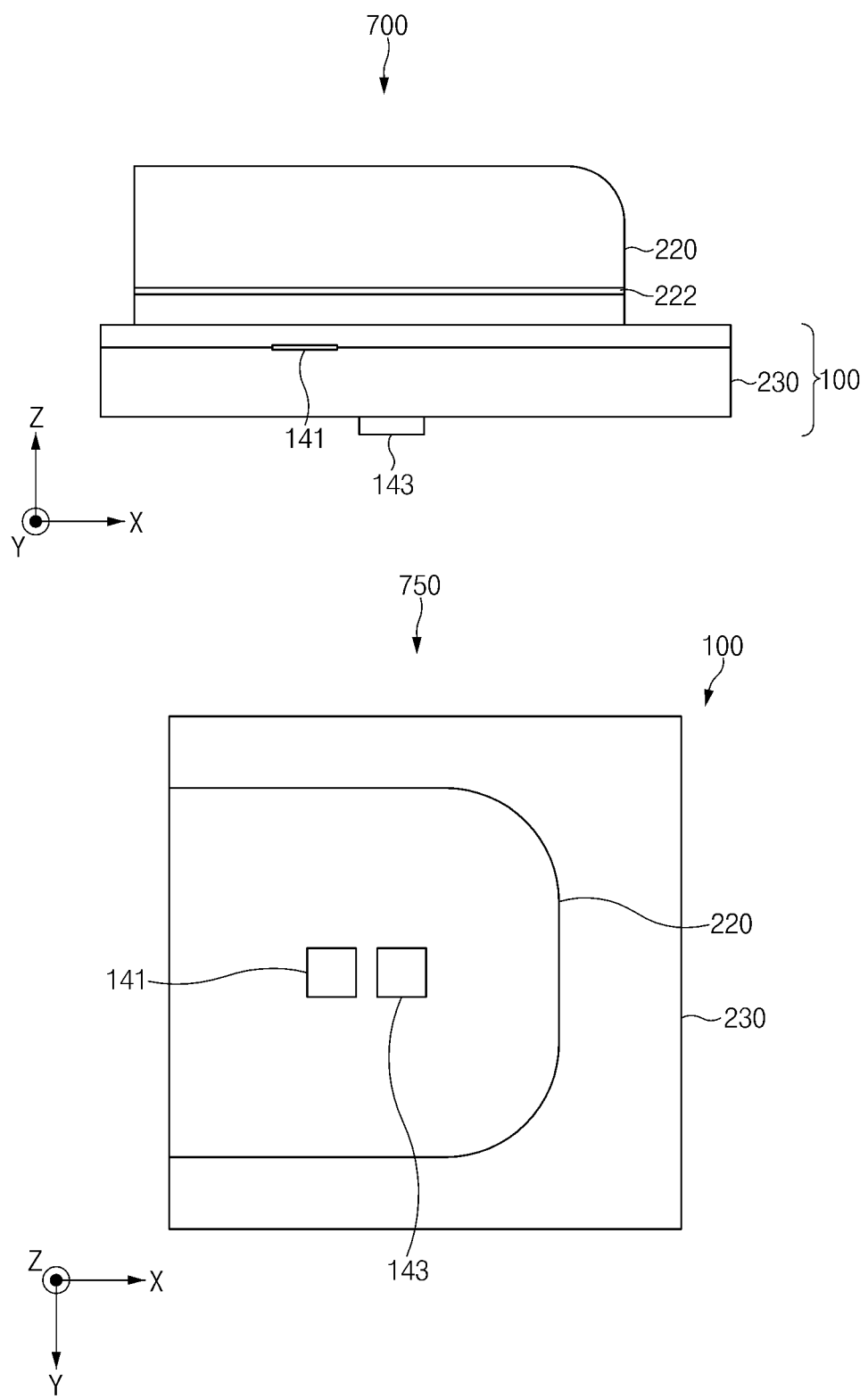
FIG. 7 is a diagram illustrating an electronic device not including an ultrasonic device acquires a PPG signal from an object according to an embodiment of the disclosure.

FIG. 7 is diagrams 700 and 750 illustrating an electronic device not including an ultrasonic device acquires a PPG signal from an object according to an embodiment of the disclosure.

Referring to FIG. 7, it illustrates that a PPG signal acquisition electronic device of the related art acquires a PPG signal from an object. FIG. 7 includes the side cross-sectional view 700 and the projection plan view 750 showing that the electronic device 100 acquires the PPG signal from the object 220.

Referring to FIG. 7, in the electronic device 100, the light detector 143 may be disposed on the bottom face of the display panel 230, and the light source 141 may be disposed on the top face of the display panel 230. According to an embodiment of the disclosure, the light source 141 may be embodied as organic light emitting diode (OLED). However, the disclosure is not limited thereto. For example, FIG. 7 is a diagram showing an embodiment of the electronic device that uses the light source of the display as the light source of the PPG sensor.

Hereinafter, with reference to FIGS. 8 and 9, an arrangement structure of components of an electronic device including an ultrasonic device and a state of the blood vessel 222 when the electronic device acquires a PPG signal will be described.

Figure 8:
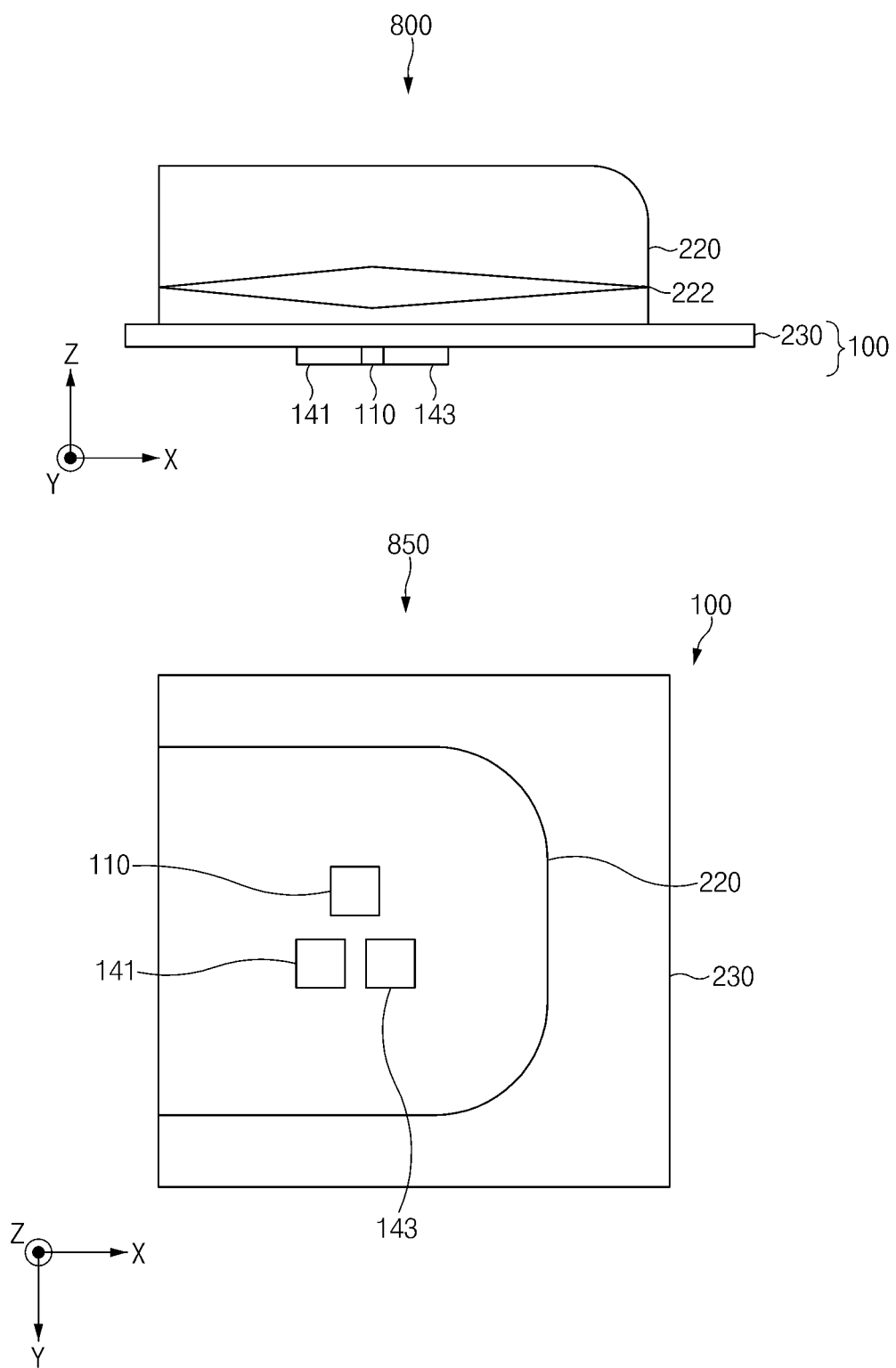
FIG. 8 is a diagram illustrating an electronic device including an ultrasonic device acquires a PPG signal from an object according to an embodiment of the disclosure.

FIG. 8 is diagrams 800 and 850 illustrating an electronic device including an ultrasonic device acquires a PPG signal from an object according to an embodiment of the disclosure.

Referring to FIG. 8, according to an embodiment of the disclosure, the electronic device 100 of FIG. 8 may be the electronic device 100 of FIG. 1. FIG. 8 includes the side cross-sectional view 800 and the projection plan view 850 showing that the electronic device 100 acquires the PPG signal from the object 220.

Referring to FIG. 8, in the electronic device 100, the light source 141 and the light detector 143 may be arranged side by side and may be disposed on the bottom face of the display panel 230. Further, in the electronic device 100, the ultrasonic device 110 may be disposed on the bottom face of the display panel 230. On one face (an XY plane in FIG. 8) of the display panel 230, the ultrasonic device 110 may be disposed between the light source 141 and the light detector 143. In the electronic device 100 according to an embodiment as shown in FIG. 8, the ultrasonic device 110, the light source 141 and the light detector 143 may be arranged along the same plane (the XY plane in FIG. 8). In a view toward at least one side face (in a Y axis direction in FIG. 8), the ultrasonic device 110 may be disposed between the light source 141 and the light detector 143.

According to an embodiment of the disclosure, the ultrasonic device 110, the light source 141, and/or the light detector 143 may not be arranged along the same plane (the XY plane in FIG. 8) but may be spaced apart from each other in a Z-axis direction.

According to an embodiment of the disclosure, in the electronic device 100, spacings between the light source 141, the light detector 143, and the ultrasonic device 110 may be adjusted such that a difference between a position of the object 220 or the blood vessel 222 inside the object to which light from the light source 141 is irradiated, and a position of the object 220 or the blood vessel 222 inside the object to which the ultrasonic wave from the ultrasonic device 110 is irradiated is within a preset error range.

According to an embodiment of the disclosure, an ultrasonic wave emitted from the ultrasonic device 110 may expand the blood vessel 222 inside the object 220. According to an embodiment of the disclosure, the light detector 143 detects light reflected from the object 220 in an expanded state of the blood vessel 222. Thus, the electronic device may acquire the PPG signal in which the magnitude of the signal component (the AC component) is increased, compared to that in a case in which the PPG signal is acquired without the action of the ultrasonic wave. In the electronic device 100 according to an embodiment of the disclosure, the ultrasonic device 110 may be disposed between the light source 141 and the light detector 143 in a view toward one face of the display panel 230. Thus, when the electronic device 100 acquires the PPG signal, the blood vessel expansion effect by the ultrasonic waves may be maximized.

Figure 9:
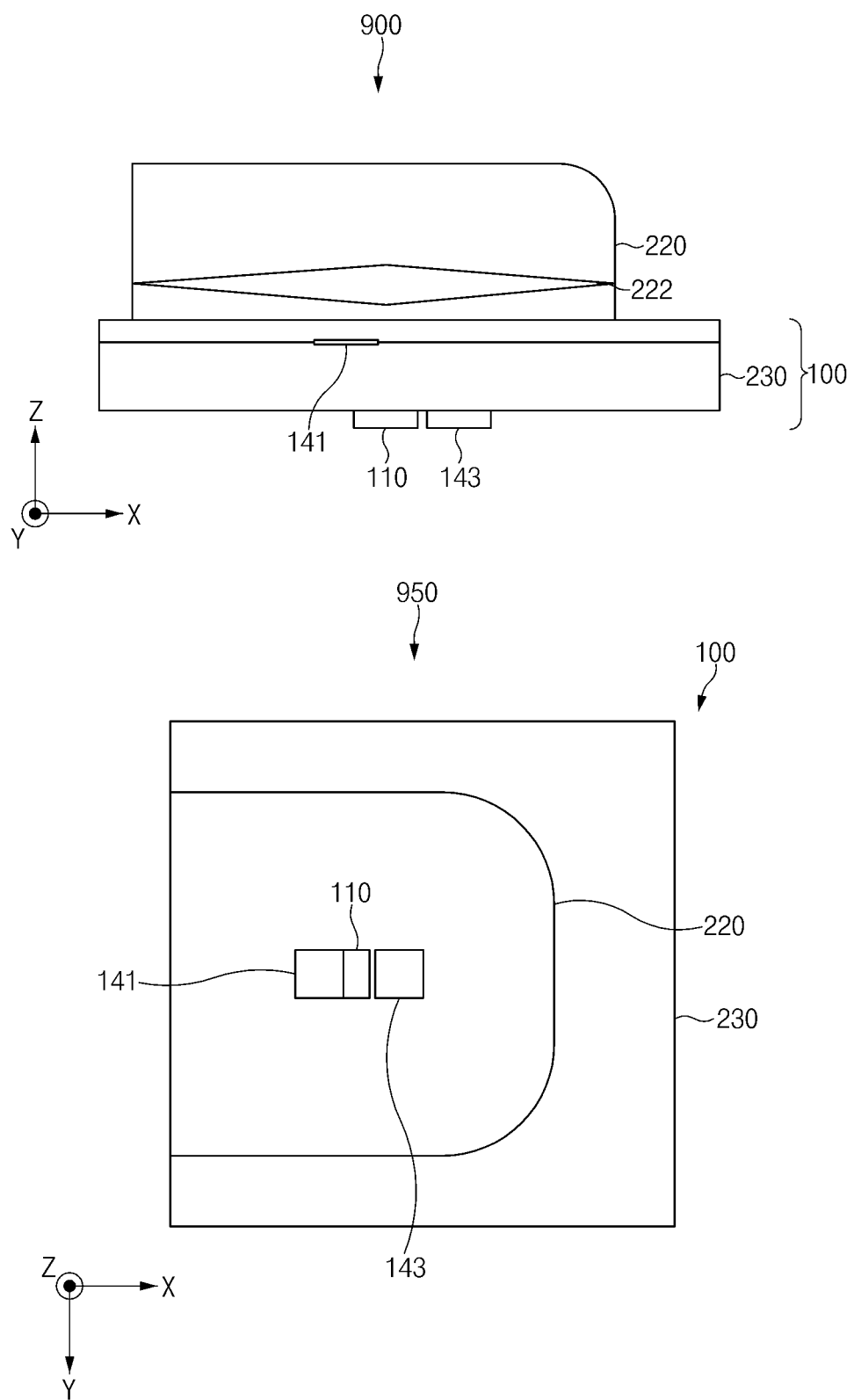
FIG. 9 is a diagram illustrating an electronic device including an ultrasonic device acquires a PPG signal from an object, according to an embodiment of the disclosure.

FIG. 9 illustrates diagrams 900 and 950 showing that an electronic device including an ultrasonic device acquires a PPG signal from an object, according to an embodiment of the disclosure. According to an embodiment of the disclosure, the electronic device 100 of FIG. 9 may be the electronic device 100 of FIG. 1. FIG. 9 includes the side cross-sectional view 900 and the projection plan view 950 showing that the electronic device 100 acquires the PPG signal from the object 220.

Referring to FIG. 9, in the electronic device 100, the light detector 143 may be disposed on the bottom face of the display panel 230, and the light source 141 may be disposed on the top face of the display panel 230. According to an embodiment of the disclosure, the light source 141 may be embodied as the organic light emitting diode (OLED). However, the disclosure is not limited thereto. For example, FIG. 9 is a diagram showing an embodiment of an electronic device that uses the light source of the display as the light source of the PPG sensor.

Further, in the electronic device 100, the ultrasonic device 110 may be disposed on the bottom face of the display panel 230. In a view toward one face (an XY plane in FIG. 9) of the display panel 230, the ultrasonic device 110 may be disposed between the light source 141 and the light detector 143. In the electronic device 100 according to an embodiment as shown in FIG. 9, the ultrasonic device 110 and the light detector 143 may be arranged along the same plane (the XY plane in FIG. 9). In a view toward at least one side face (in a Z axis direction in FIG. 9), the ultrasonic device 110 may be disposed between the light source 141 and the light detector 143.

Since FIG. 9 is structurally different from FIG. 8 only in terms of a position in the Z axis of the light source 141, the descriptions referring to FIG. 8 may be equally applied to an effect of the electronic device 100 as shown in FIG. 9 on the blood vessel 222 of the object 220 and a resulting effect of improving the quality of the PPG signal.

Hereinafter, with reference to FIGS. 10 and 11, an arrangement structure of components of an electronic device including a circular ultrasonic device and a state of the blood vessel 222 when the electronic device acquires a PPG signal will be described.

Figure 10:
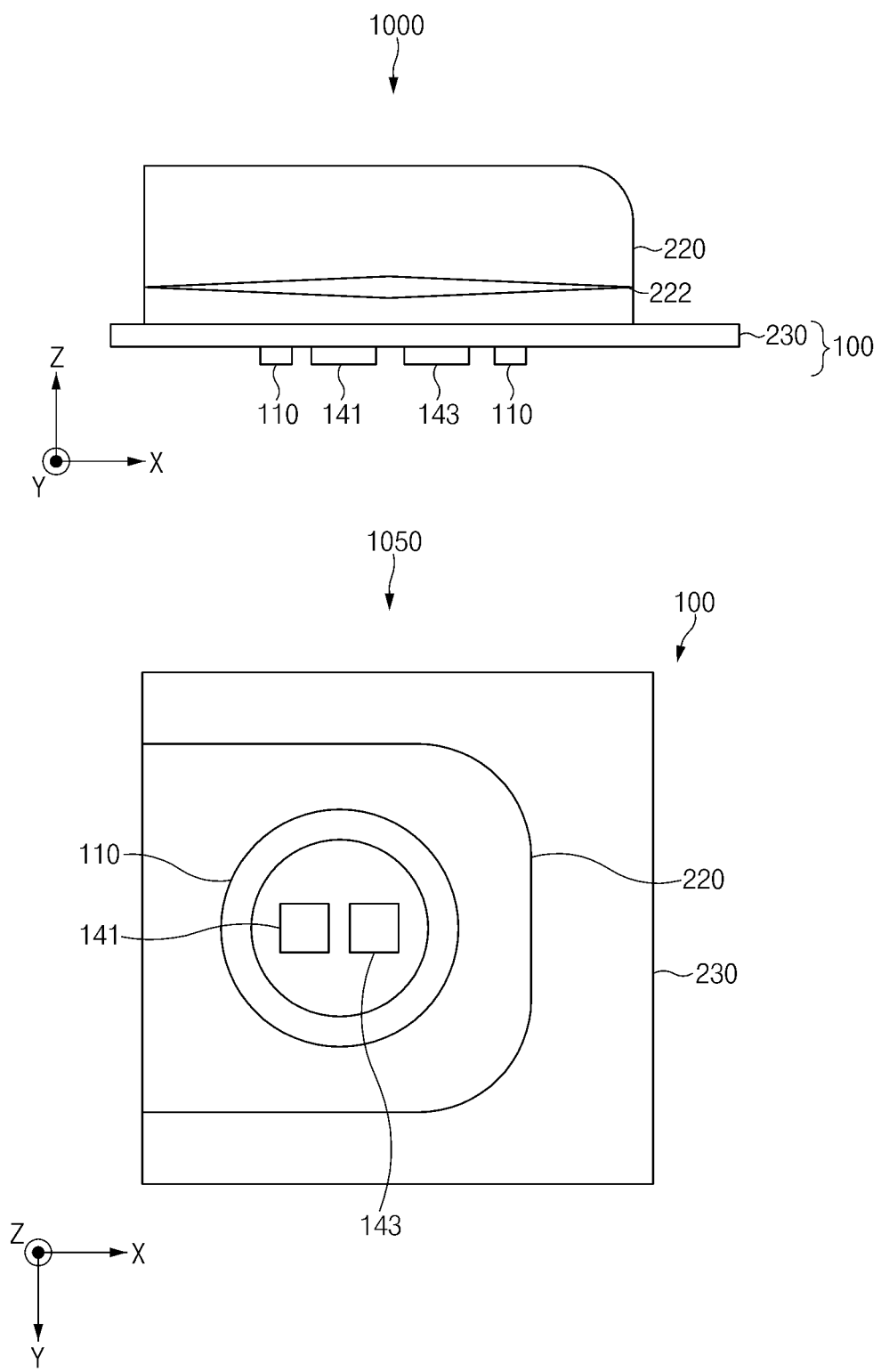
FIG. 10 is a diagram an electronic device including a circular ultrasonic device acquires a PPG signal from an object according to an embodiment of the disclosure.

FIG. 10 includes diagrams 1000 and 1050 illustrating that an electronic device including a circular ultrasonic device acquires a PPG signal from an object, according to an embodiment of the disclosure. According to an embodiment of the disclosure, the electronic device 100 of FIG. 10 may be the electronic device 100 of FIG. 1. FIG. 10 includes the side cross-sectional view 1000 and the projection plan view 1050 showing that the electronic device 100 acquires the PPG signal from the object 220.

Referring to FIG. 10, in the electronic device 100, the light source 141 and the light detector 143 may be arranged side by side and may be disposed on the bottom face of the display panel 230. According to an embodiment of the disclosure, the electronic device 100 may include the circular ultrasonic device 110. The circular ultrasonic device 110 may be disposed on the bottom face of the display panel 230. In a view toward one face (an XY plane in FIG. 10) of the display panel 230, a center of the circular ultrasonic device 110 may be positioned at a median point between the light source 141 and the light detector 143.

Referring to FIG. 10, in the electronic device 100 according to an embodiment of the disclosure, the ultrasonic device 110 having a ring structure including a hollow space defined therein may be disposed to surround the light source 141 and the light detector 143. According to an embodiment of the disclosure, the center of the ultrasonic device 110 may be positioned at a median point between the light source 141 and the light detector 143. According to an embodiment of the disclosure, the electronic device 100 may be configured such that the center of the ultrasonic device 110 is positioned in an area between the light source 141 and the light detector 143.

In one example, FIG. 10 illustrates a case in which the ultrasonic device 110 is circular. However, the disclosure is not limited thereto, and a planar shape of the ultrasonic device 110 may include a polygonal shape. The circular or polygonal ultrasonic device 110 may have a structure in which a plurality of ultrasonic wave generators are consecutively arranged in a pixel structure. The electronic device 100 according to an embodiment of the disclosure may operably control the plurality of ultrasonic wave generators to act as a single ultrasonic device 110. In the electronic device 100 according to an embodiment of the disclosure, the center of the ultrasonic device 110 may be positioned at a median point between the light source 141 and the light detector 143 in a view toward one face (the XY plane in FIG. 10) of the display panel 230. Thus, when the PPG signal is acquired, the blood vessel expansion effect by the ultrasonic waves may be maximized. According to an embodiment of the disclosure, the center of the ultrasonic device 110 including the plurality of ultrasonic wave generators may be a focal point of beam forming of the ultrasonic waves emitted from the plurality of ultrasonic wave generators. According to an embodiment of the disclosure, the plurality of ultrasonic wave generators may be arranged such that the focal point of the beam forming of the ultrasonic waves emitted from the plurality of ultrasonic wave generators included in the ultrasonic device 110 may be positioned at a median point between the light source 141 and the light detector 143 in a view toward one face (the XY plane in FIG. 10) of the display panel 230.

Figure 11:
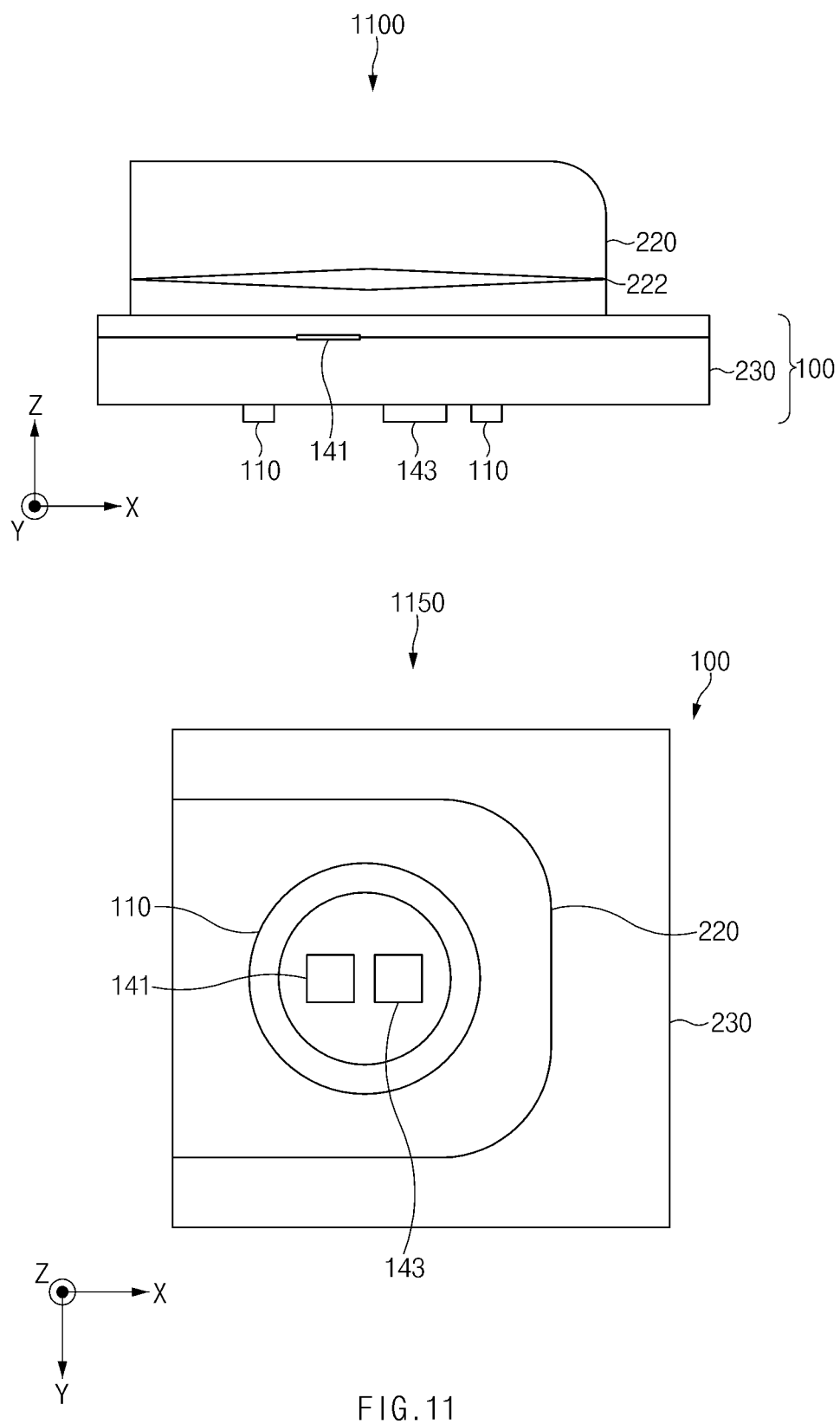
FIG. 11 is a diagram illustrating an electronic device including a circular ultrasonic device acquires a PPG signal from an object according to an embodiment of the disclosure.

FIG. 11 is a diagram illustrating an electronic device including a circular ultrasonic device acquires a PPG signal from an object according to an embodiment of the disclosure. According to an embodiment of the disclosure, the electronic device 100 of FIG. 11 may be the electronic device 100 of FIG. 1. FIG. 11 includes a side cross-sectional view 1100 and a projection plan view 1150 showing that the electronic device 100 acquires the PPG signal from the object 220.

Referring to FIG. 11, in the electronic device 100, the light detector 143 may be disposed on the bottom face of the display panel 230, and the light source 141 may be disposed on the top face of the display panel 230. According to an embodiment of the disclosure, the light source 141 may be embodied as the OLED. However, the disclosure is not limited thereto. For example, FIG. 11 is a diagram showing an embodiment of an electronic device that uses the light source of the display as the light source of the PPG sensor.

According to an embodiment of the disclosure, the electronic device 100 may include the circular ultrasonic device 110. The circular ultrasonic device 110 may be disposed on the bottom face of the display panel 230. In FIG. 11, a center of the circular ultrasonic device 110 may be positioned at a median point between the light source 141 and the light detector 143 in a view toward one face (the XY plane in FIG. 11) of the display panel 230.

Referring to FIG. 11, in the electronic device 100 according to an embodiment of the disclosure, the ultrasonic device 110 having a ring structure including a hollow space defined therein may be disposed to surround the light source 141 and the light detector 143. According to an embodiment of the disclosure, the center of the ultrasonic device 110 may be positioned at a median point between the light source 141 and the light detector 143 in a view toward one face (the XY plane in FIG. 11) of the display panel 230.

Since FIG. 11 is structurally different from FIG. 10 only in terms of a position in the Z axis of the light source 141, the descriptions referring to FIG. 10 may be equally applied to an effect of the electronic device 100 as shown in FIG. 11 on the blood vessel 222 of the object 220 and a resulting effect of improving the quality of the PPG signal.

Hereinafter, with reference to FIGS. 12 and 13, an arrangement structure of components of an electronic device including an ultrasonic device including a plurality of ultrasonic wave generators and a state of the blood vessel 222 when the electronic device acquires the PPG signal will be described.

Figure 12:
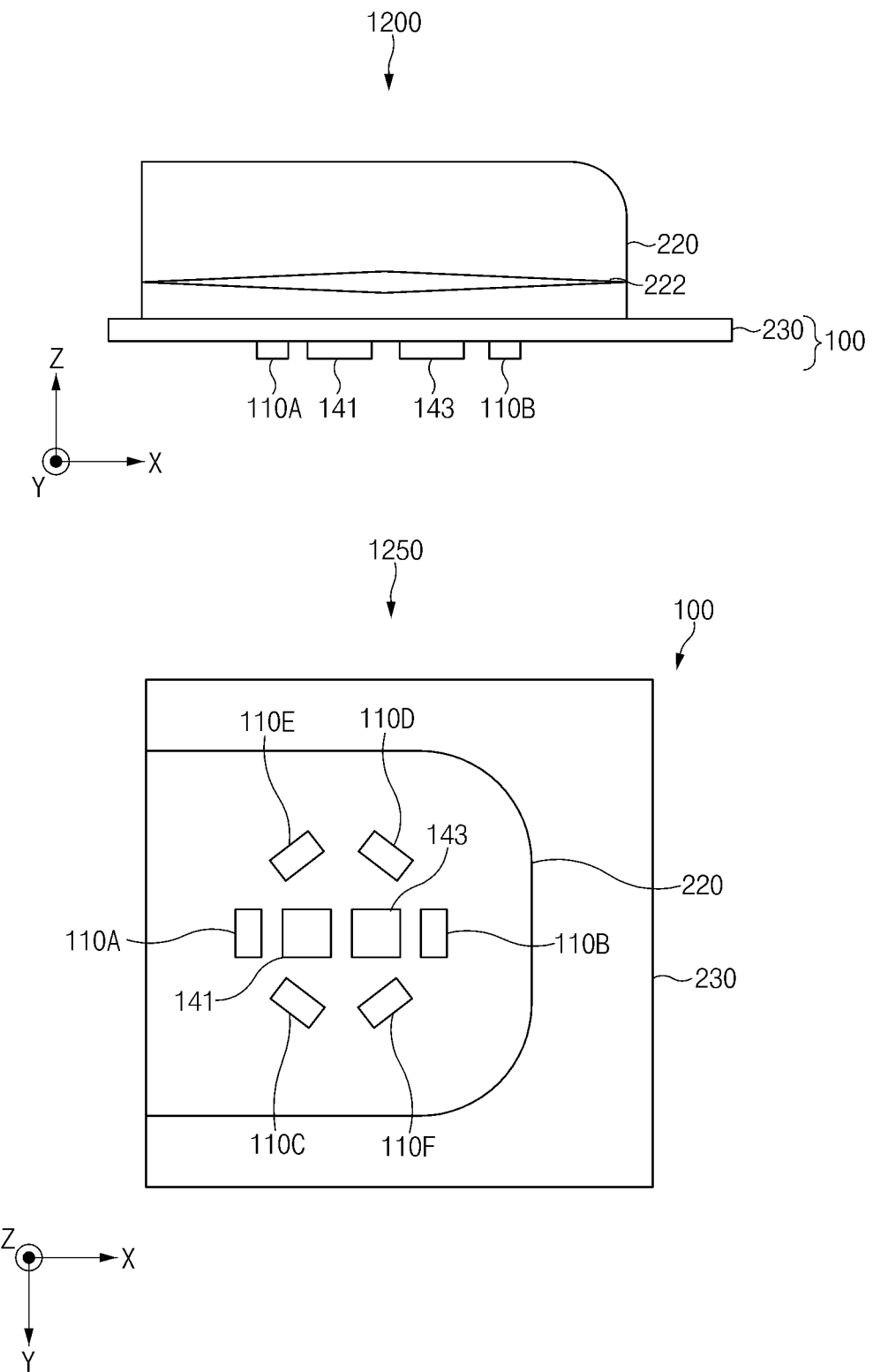
FIG. 12 is a diagram illustrating an electronic device including an ultrasonic device including a plurality of ultrasonic wave generators acquires a PPG signal from an object according to an embodiment of the disclosure.

FIG. 12 includes diagrams 1200 and 1250 illustrating that an electronic device including an ultrasonic device including a plurality of ultrasonic wave generators acquires a PPG signal from an object according to an embodiment of the disclosure. According to an embodiment of the disclosure, the electronic device 100 of FIG. 12 may be the electronic device 100 of FIG. 1. FIG. 12 includes the side cross-sectional view 1200 and the projection plan view 1250 showing that the electronic device 100 acquires the PPG signal from the object 220.

Referring to FIG. 12, in the electronic device 100, the light source 141 and the light detector 143 may be arranged side by side and may be disposed on the bottom face of the display panel 230. According to an embodiment of the disclosure, the electronic device 100 may include a plurality of ultrasonic wave generators 110A, 110B, 110C, 110D, 110E, and 110F. The plurality of ultrasonic wave generators 110A, 110B, 110C, 110D, 110E, and 110F may be disposed on the bottom face of the display panel 230. A center of an arrangement of the plurality of ultrasonic wave generators 110A, 110B, 110C, 110D, 110E, and 110F may be positioned at a median point between the light source 141 and the light detector 143 in a view toward one face (the XY plane in FIG. 12) of the display panel 230.

Referring to FIG. 12, in the electronic device 100 according to an embodiment of the disclosure, the plurality of ultrasonic wave generators 110A, 110B, 110C, 110D, 110E, and 110F may be arranged to surround the light source 141 and the light detector 143. According to an embodiment of the disclosure, the center of the arrangement of the plurality of ultrasonic wave generators 110A, 110B, 110C, 110D, 110E, and 110F may be positioned at a median point between the light source 141 and the light detector 143. In one example, FIG. 12 illustrates a case where six ultrasonic wave generators are arranged in a hexagonal manner. However, the disclosure is not limited thereto, and various numbers of ultrasonic wave generators may be arranged in various shapes.

In the electronic device 100 according to an embodiment of the disclosure, the center of the arrangement of the plurality of ultrasonic wave generators 110A, 110B, 110C, 110D, 110E, and 110F may be positioned at a median point between the light source 141 and the light detector 143 in a view toward one face (the XY plane in FIG. 12) of the display panel 230. Thus, when measuring the PPG signal, the maximum blood vessel expansion effect by the ultrasonic waves may be realized.

According to an embodiment of the disclosure, when the center of the arrangement of the plurality of ultrasonic wave generators 110A, 110B, 110C, 110D, 110E, and 110F is positioned in an area between the light source 141 and the light detector 143 in a view toward one face (the XY plane in FIG. 12) of the display panel 230, a phase of a first ultrasonic wave emitted from the first ultrasonic wave generator 110A, a phase of a second ultrasonic wave emitted from the second ultrasonic wave generator 110B, a phase of a third ultrasonic wave emitted from the third ultrasonic wave generator 110C, a phase of a fourth ultrasonic wave emitted from the fourth ultrasonic wave generator 110D, a phase of a fifth ultrasonic wave emitted from the fifth ultrasonic wave generator 110E, and a phase of a sixth ultrasonic wave emitted from the sixth ultrasonic wave generator 110F may be set to be equal to each other.

In other words, when the center of the arrangement of the plurality of ultrasonic wave generators 110A, 110B, 110C, 110D, 110E, and 110F is positioned in an area between the light source 141 and the light detector 143 in a view toward one face (the XY plane in FIG. 12) of the display panel 230, the phases of the ultrasonic waves respectively generated from the plurality of ultrasonic wave generators 110A, 110B, 110C, 110D, 110E, and 110F may be set to be in-phase with each other.

Figure 13:
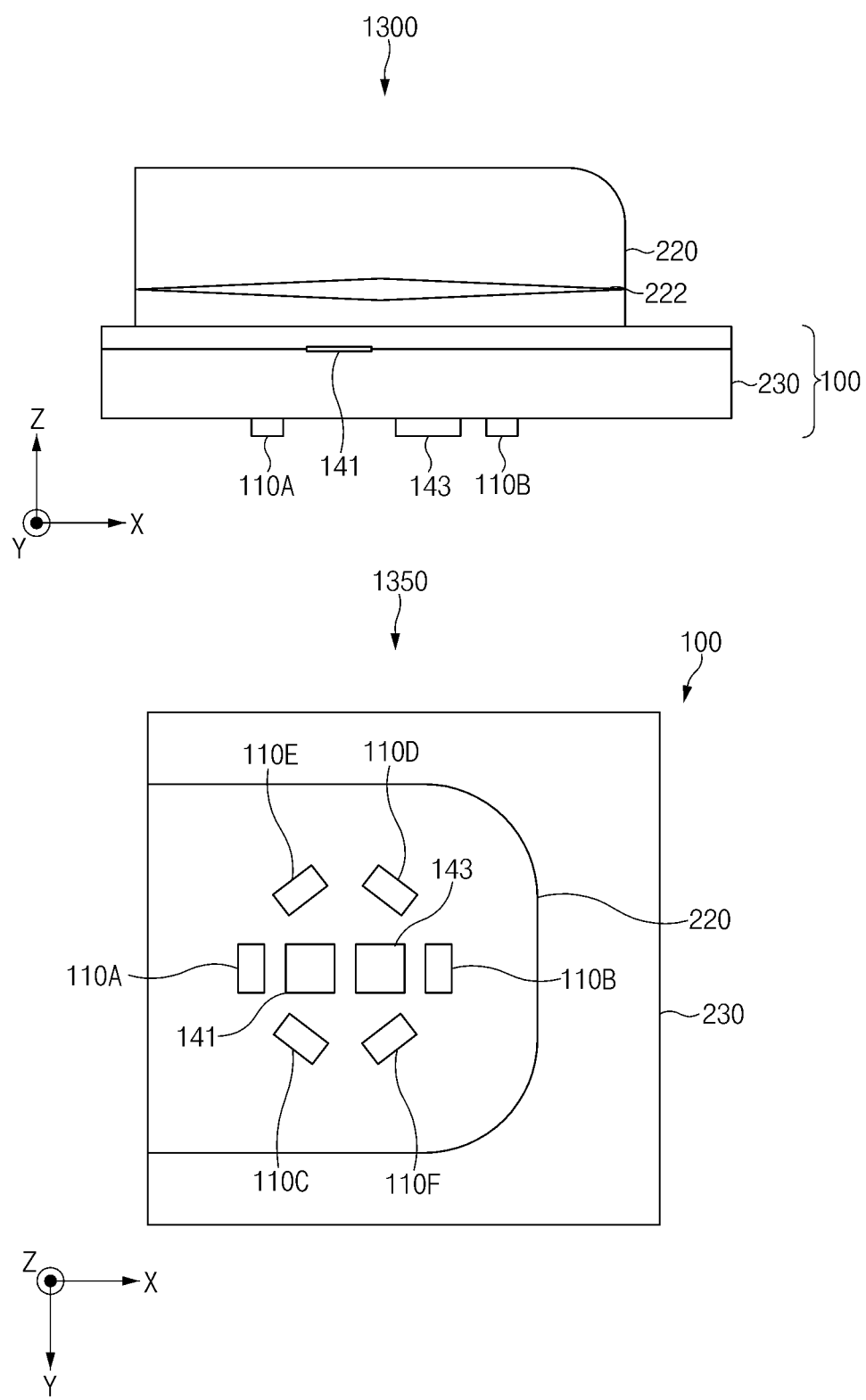
FIG. 13 is a diagram illustrating an electronic device including an ultrasonic device including a plurality of ultrasonic wave generators acquires a PPG signal from an object according to an embodiment of the disclosure.

FIG. 13 includes diagrams 1300 and 1350 illustrating an electronic device including an ultrasonic device including a plurality of ultrasonic wave generators acquires a PPG signal from an object, according to an embodiment of the disclosure. According to an embodiment of the disclosure, the electronic device 100 of FIG. 13 may be the electronic device 100 of FIG. 1. FIG. 13 includes the side cross-sectional view 1300 and the projection plan view 1350 showing that the electronic device 100 acquires the PPG signal from the object 220.

Referring to FIG. 13, in the electronic device 100, the light detector 143 may be disposed on the bottom face of the display panel 230, and the light source 141 may be disposed on the top face of the display panel 230. According to an embodiment of the disclosure, the light source 141 may be embodied as the OLED. However, the disclosure is not limited thereto. For example, FIG. 13 is a diagram showing an embodiment of an electronic device that uses the light source of the display as the light source of the PPG sensor.

According to an embodiment of the disclosure, the ultrasonic device of the electronic device 100 (e.g., the ultrasonic device 110 of FIG. 1) may include a plurality of ultrasonic wave generators 110A, 110B, 110C, 110D, 110E, and 110F. The plurality of ultrasonic wave generators 110A, 110B, 110C, 110D, 110E, and 110F may be disposed on the bottom face of the display panel 230. A center of an arrangement of the plurality of ultrasonic wave generators 110A, 110B, 110C, 110D, 110E, and 110F may be positioned at a median point between the light source 141 and the light detector 143 in a view toward one face (the XY plane in FIG. 13) of the display panel 230.

Referring to FIG. 13, in the electronic device 100 according to an embodiment of the disclosure, the plurality of ultrasonic wave generators 110A, 110B, 110C, 110D, 110E, and 110F may be arranged to surround the light source 141 and the light detector 143. According to an embodiment of the disclosure, the center of the arrangement of the plurality of ultrasonic wave generators 110A, 110B, 110C, 110D, 110E, and 110F may be positioned at a median point between the light source 141 and the light detector 143.

According to an embodiment of the disclosure, when the center of the arrangement of the plurality of ultrasonic wave generators 110A, 110B, 110C, 110D, 110E, and 110F is positioned in an area between the light source 141 and the light detector 143 in a view toward one face (the XY plane in FIG. 13) of the display panel 230, the phases of the ultrasonic waves respectively generated from the plurality of ultrasonic wave generators 110A, 110B, 110C, 110D, 110E, and 110F may be set to be in-phase with each other.

Since FIG. 13 is structurally different from FIG. 12 only in terms of a position in the Z axis of the light source 141, the descriptions referring to FIG. 12 may be equally applied to an effect of the electronic device 100 as shown in FIG. 13 on the blood vessel 222 of the object 220 and a resulting effect of improving the quality of the PPG signal.

Hereinafter, with reference to FIGS. 14 and 15, an arrangement structure of components of an electronic device including an ultrasonic device including a plurality of ultrasonic wave generators which are arranged in an asymmetric manner, and a state of a blood vessel when the electronic device acquires a PPG signal will be described.

Figure 14:
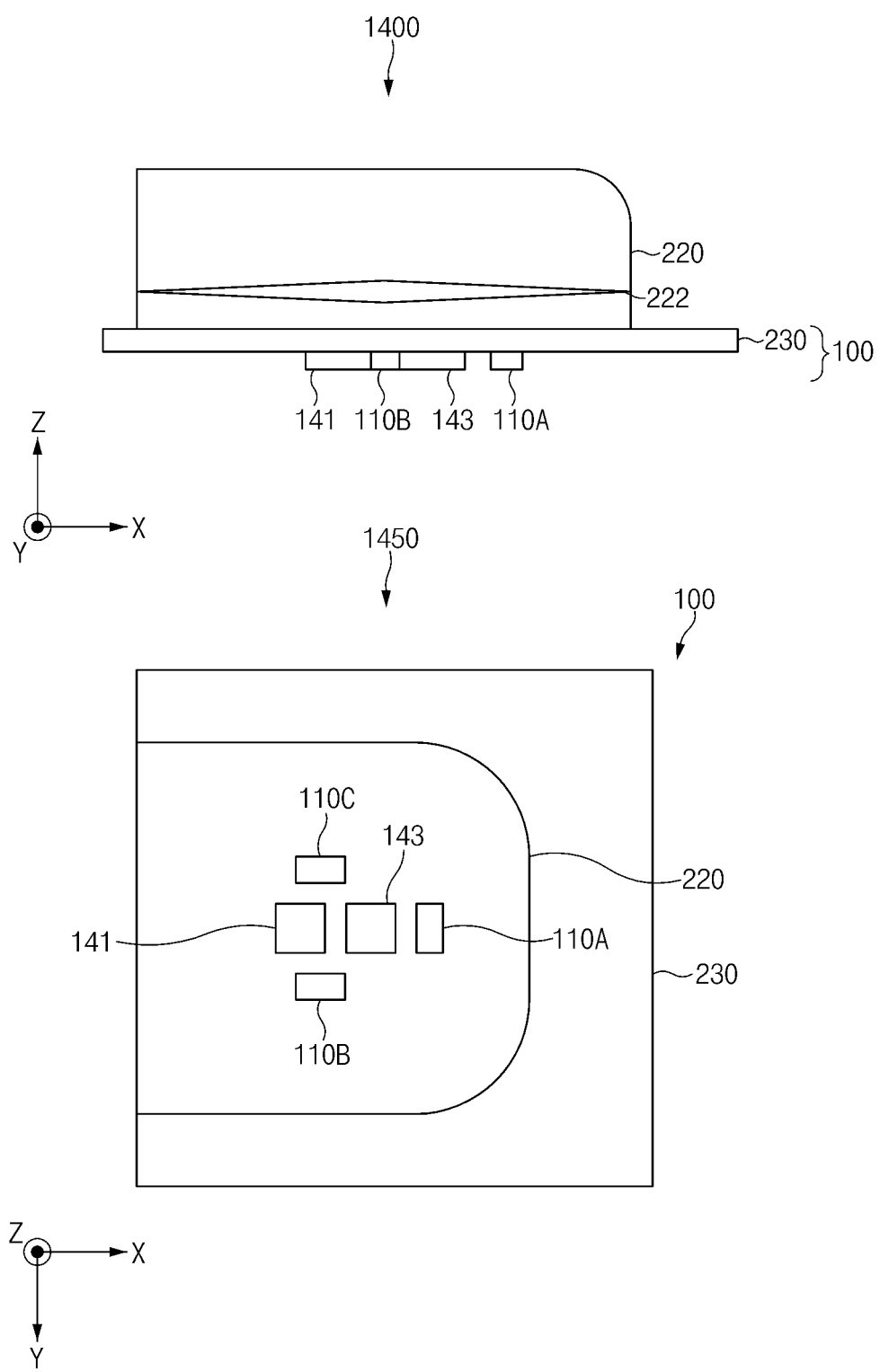
FIG. 14 is a diagram illustrating an electronic device including an ultrasonic device including a plurality of ultrasonic wave generators acquires a PPG signal from an object according to an embodiment of the disclosure.

FIG. 14 includes diagrams 1400 and 1450 illustrating an electronic device including an ultrasonic device including a plurality of ultrasonic wave generators acquires a PPG signal from an object, according to an embodiment of the disclosure. According to an embodiment of the disclosure, the electronic device 100 of FIG. 14 may be the electronic device 100 of FIG. 1. FIG. 14 includes the side cross-sectional view 1400 and the projection plan view 1450 showing that the electronic device 100 acquires the PPG signal from the object 220.

Referring to FIG. 14, in the electronic device 100, the light source 141 and the light detector 143 may be arranged side by side and may be disposed on the bottom face of the display panel 230. According to an embodiment of the disclosure, the electronic device 100 may include a plurality of ultrasonic wave generators 110A, 110B, and 110C. The plurality of ultrasonic wave generators 110A, 110B, and 110C may be disposed on the bottom face of the display panel 230.

In the electronic device 100 according to an embodiment of the disclosure, the plurality of ultrasonic wave generators 110A, 110B, and 110C may be arranged such that a focal point of beam forming of the ultrasonic waves emitted from the ultrasonic device (e.g., the ultrasonic device 110 in FIG. 1) including the plurality of ultrasonic wave generators 110A, 110B, and 110C may be positioned at a median point between the light source 141 and the light detector 143 in a view toward one face (the XY plane in FIG. 14) of the display panel 230.

According to an embodiment of the disclosure, the electronic device 100 may control phases of ultrasonic waves emitted from the plurality of ultrasonic wave generators 110A, 110B, and 110C, respectively. According to an embodiment of the disclosure, the electronic device 100 may control the plurality of ultrasonic wave generators 110A, 110B, and 110C such that the first ultrasonic wave generator 110A may emit a first ultrasonic wave, the second ultrasonic wave generator 110B may emit a second ultrasonic wave, and the third ultrasonic wave generator 110C may emit a third ultrasonic wave. According to an embodiment of the disclosure, the electronic device 100 may control a phase of the first ultrasonic wave, a phase of the second ultrasonic wave, and a phase of the third ultrasonic wave such that the first ultrasonic wave, the second ultrasonic wave, and the third ultrasonic wave are emitted toward a focal point positioned between the light source 141 and the light detector 143.

In one example, beam forming technology may be applied to the plurality of ultrasonic wave generators 110A, 110B, and 110C. According to an embodiment of the disclosure, the electronic device 100 may form a beam based on the first ultrasonic wave, the second ultrasonic wave, and the third ultrasonic wave. Therefore, the electronic device 100 according to an embodiment of the disclosure may control the phase of the first ultrasonic wave, the phase of the second ultrasonic wave, and the phase of the third ultrasonic wave such that a focal point of the beam forming based on the first ultrasonic wave, the second ultrasonic wave, and the third ultrasonic wave is positioned at a median point between the light source 141 and the light detector 143.

According to an embodiment of the disclosure, when a center of an arrangement of the plurality of ultrasonic wave generators 110A, 110B, and 110C is positioned at a median point between the light source 141 and the light detector 143, the electronic device 100 may control the phase of the first ultrasonic wave, the phase of the second ultrasonic wave, and the phase of the third ultrasonic wave so as to be in-phase with each other.

In another example, when the center of the arrangement of the plurality of ultrasonic wave generators 110A, 110B, and 110C is not positioned at a median point between the light source 141 and the light detector 143, the electronic device 100 may control the phase of the first ultrasonic wave, the phase of the second ultrasonic wave, and the phase of the third ultrasonic wave such that at least some of the phase of the first ultrasonic wave, the phase of the second ultrasonic wave, and the phase of the third ultrasonic wave are out-of-phase with each other. According to an embodiment of the disclosure, the electronic device 100 may apply a phase delay to at least some of the phase of the first ultrasonic wave, the phase of the second ultrasonic wave, and the phase of the third ultrasonic wave such that at least some of the phase of the first ultrasonic wave, the phase of the second ultrasonic wave, and the phase of the third ultrasonic wave are out-of-phase with each other.

Figure 15:
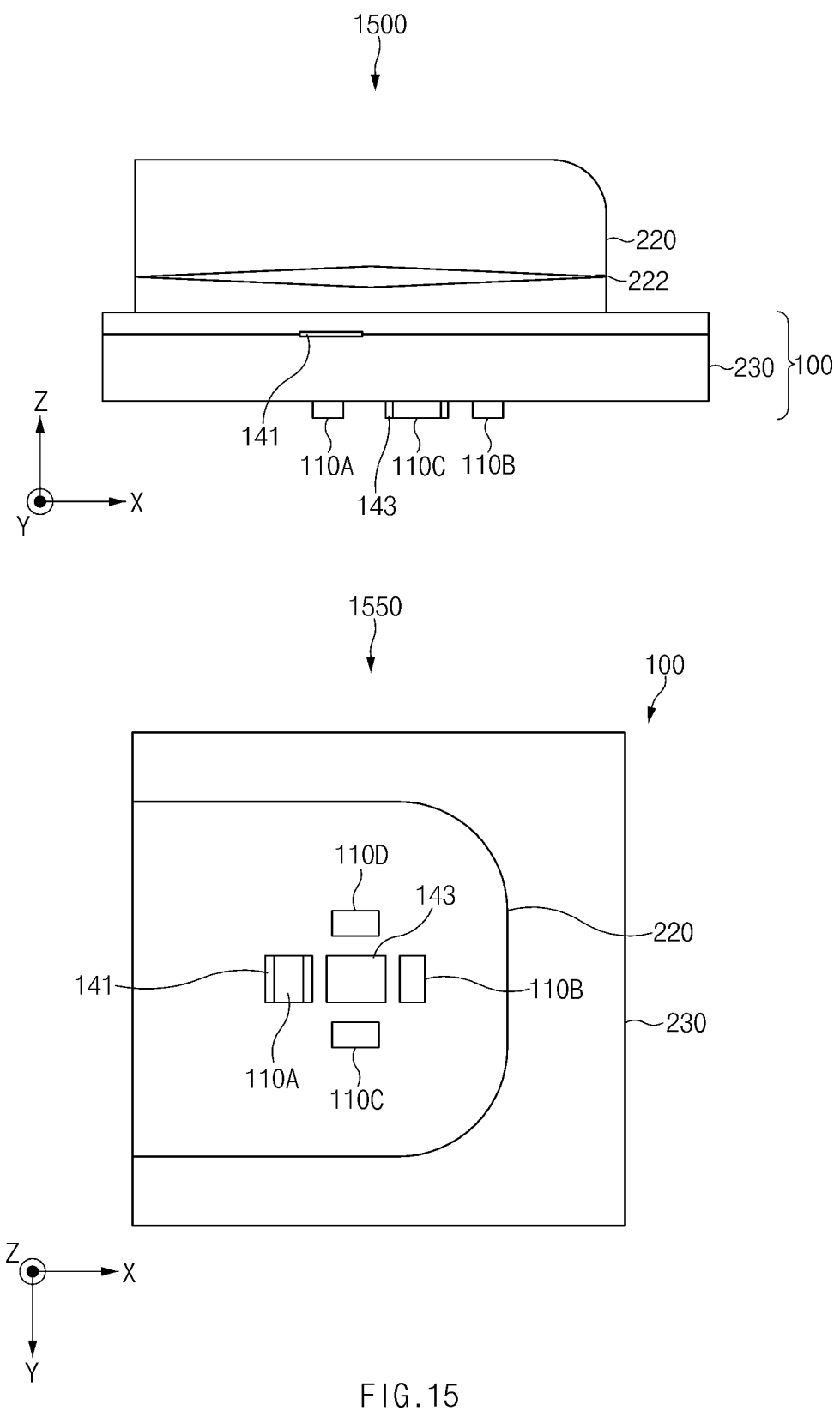
FIG. 15 is a diagram illustrating an electronic device including an ultrasonic device including a plurality of ultrasonic wave generators acquires a PPG signal from an object according to an embodiment of the disclosure.

FIG. 15 includes diagrams 1500 and 1550 illustrating that an electronic device including an ultrasonic device including a plurality of ultrasonic wave generators acquires a PPG signal from an object, according to an embodiment of the disclosure. According to an embodiment of the disclosure, the electronic device 100 of FIG. 15 may be the electronic device 100 of FIG. 1. FIG. 15 includes the side cross-sectional view 1500 and the projection plan view 1550 showing that the electronic device 100 acquires the PPG signal from the object 220.

Referring to FIG. 15, in the electronic device 100, the light detector 143 may be disposed on the bottom face of the display panel 230, and the light source 141 may be disposed on the top face of the display panel 230. According to an embodiment of the disclosure, the light source 141 may be embodied as the OLED. However, the disclosure is not limited thereto. For example, FIG. 15 is a diagram showing an embodiment of an electronic device that uses the light source of the display as the light source of the PPG sensor.

According to an embodiment of the disclosure, the ultrasonic device of the electronic device 100 (e.g., the ultrasonic device 110 of FIG. 1) may include a plurality of ultrasonic wave generators 110A, 110B, 110C, and 110D. The plurality of ultrasonic wave generators 110A, 110B, 110C, and 110D may be disposed on the bottom face of the display panel 230.

In one example, the electronic device 100 according to an embodiment may control phases of ultrasonic waves emitted from the plurality of ultrasonic wave generators 110A, 110B, 110C, and 110D, respectively. According to an embodiment of the disclosure, the electronic device 100 may control the plurality of ultrasonic wave generators 110A, 110B, 110C, and 110D such that the first ultrasonic wave generator 110A may emit a first ultrasonic wave, the second ultrasonic wave generator 110B may emit a second ultrasonic wave, the third ultrasonic wave generator 110C may emit a third ultrasonic wave and the fourth ultrasonic wave generator 110D may emit a fourth ultrasonic wave. According to an embodiment of the disclosure, the electronic device 100 may control a phase of the first ultrasonic wave, a phase of the second ultrasonic wave, a phase of the third ultrasonic wave, and a phase of the fourth ultrasonic wave such that the first ultrasonic wave, the second ultrasonic wave, the third ultrasonic wave, and the fourth ultrasonic wave are emitted toward a focal point located between the light source 141 and the light detector 143.

As described above, the beam forming technology may be applied to the plurality of ultrasonic wave generators 110A, 110B, 110C, and 110D. According to an embodiment of the disclosure, the electronic device 100 may form a beam based on the first ultrasonic wave, the second ultrasonic wave, the third ultrasonic wave, and the fourth ultrasonic wave. Therefore, the electronic device 100 according to an embodiment of the disclosure may control the phase of the first ultrasonic wave, the phase of the second ultrasonic wave, the phase of the third ultrasonic wave, and the phase of the fourth ultrasonic wave such that a focal point of the beam forming based on the first ultrasonic wave, the second ultrasonic wave, the third ultrasonic wave, and the fourth ultrasonic wave is positioned at a median point between the light source 141 and the light detector 143.

Referring to FIG. 15, the electronic device 100 according to an embodiment may have a structure in which a center of an arrangement of the plurality of ultrasonic wave generators 110A, 110B, 110C, and 110D is not positioned at a median point between the light source 141 and the light detector 143. In this case, the electronic device 100 may control the phase of the first ultrasonic wave, the phase of the second ultrasonic wave, the phase of the third ultrasonic wave, and the phase of the fourth ultrasonic wave such that at least some of the phase of the first ultrasonic wave, the phase of the second ultrasonic wave, the phase of the third ultrasonic wave, and the phase of the fourth ultrasonic wave are out-of-phase with each other. According to an embodiment of the disclosure, the electronic device 100 may apply a phase delay to at least some of the phase of the first ultrasonic wave, the phase of the second ultrasonic wave, the phase of the third ultrasonic wave, and the phase of the fourth ultrasonic wave such that at least some of the phase of the first ultrasonic wave, the phase of the second ultrasonic wave, the phase of the third ultrasonic wave, and the phase of the fourth ultrasonic wave are out-of-phase with each other.

In the electronic device 100 according to an embodiment as shown in FIGS. 14 and 15, the focal point of the beam forming formed based on the ultrasonic waves emitted from the plurality of ultrasonic wave generators may be positioned at a median point between the light source 141 and the light detector 143. Thus, when the PPG signal is acquired, the blood vessel expansion effect by the ultrasonic waves may be maximally acquired. In the embodiment as shown in FIG. 14, a case in which the electronic device 100 adjusts the focal point of the beam forming based on the ultrasonic waves emitted from three ultrasonic wave generators 110A, 110B, and 110C is described by way of example. In the embodiment as shown in FIG. 15, a case in which the electronic device 100 controls the focal point of the beam forming based on the ultrasonic waves emitted from the four ultrasonic wave generators 110A, 110B, 110C, and 110D is described by way of example. However, the disclosure is not limited thereto, and various numbers of ultrasonic wave generators may be arranged in various forms.

Hereinafter, with reference to FIG. 16, a user interface provided by an electronic device so as to be displayed on a display to acquire a PPG signal according to an embodiment will be described.

FIG. 16 is a diagram 1600 illustrating a user interface provided by an electronic device to acquire a PPG signal according to an embodiment of the disclosure. According to an embodiment of the disclosure, the electronic device 100 of FIG. 16 may be the electronic device 100 of FIG. 1.

Referring to a first state 1601 of FIG. 16, according to an embodiment of the disclosure, the electronic device 100 may display the first area 1610 for measuring a PPG signal on the display. The first area 1610 may be displayed so that the user may recognize the first area as being distinguished from other areas on the display. The first area 1610 may be displayed on the display when the electronic device 100 receives a user's input for executing an application for measuring the PPG signal.

For example, the first area 1610 may correspond to an area in which a touch sensor (e.g., a touch panel) corresponding to an ultrasonic device (e.g., the ultrasonic device 110 of FIG. 1) of the electronic device 100 is disposed. According to an embodiment of the disclosure, the electronic device 100 may detect an object contacting the first area 1610, and upon detecting the object, may emit the ultrasonic waves to the object using the ultrasonic device. According to an embodiment of the disclosure, when the ultrasonic device is included in a fingerprint recognition sensor, the first area 1610 may be a fingerprint recognition area.

According to an embodiment of the disclosure, in the first state 1601, the electronic device 100 may display the first area 1610 on the display as well as a guide message of "Please contact a measurement target portion with a displayed area."

According to an embodiment of the disclosure, in the first state 1601, the electronic device 100 may detect the object 220 (e.g., a user's finger) which is in contact with at least a portion of the first area 1610. According to an embodiment of the disclosure, upon detecting the object 220, the electronic device 100 may enter a second state 1602.

According to an embodiment of the disclosure, in the second state 1602, the electronic device 100 may emit the ultrasonic waves using the ultrasonic device in response to the detection of the object 220. In this case, the object 220 may be exposed to the ultrasonic waves for a predefined time duration such that the blood vessel inside the object 220 may be expanded.

According to an embodiment of the disclosure, the electronic device 100 may emit light using the light source (e.g., the light source 141 of FIG. 1) in response to the detection of the object 220. The electronic device 100 may emit the light while emitting the ultrasonic waves, or emit the ultrasonic waves and then emit the light. According to an embodiment of the disclosure, the light source may be an independent light source disposed on an area of the bottom face of the display panel corresponding to the first area 1610. In another example, the light source may be a light source (e.g., OLED) disposed on an area of the top face of the display panel corresponding to the first area 1610.

According to an embodiment of the disclosure, in the second state 1602, the electronic device 100 may detect the light reflected from the object 220 using the light detector (e.g., the light detector 143 of FIG. 1).

According to an embodiment of the disclosure, in the second state 1602, while the electronic device 100 operates at least some of the ultrasonic device, the light source, and the light detector in response to the detection of the object 220, the electronic device 100 may display a guide message of "A PPG signal is being measured. Please maintain a contact state until an end is notified" on the display.

According to an embodiment of the disclosure, the electronic device 100 disclosed in the disclosure may acquire the PPG signal based on the light detected from the object 220 whose the blood vessel has been expanded by the ultrasonic waves, thereby acquiring the PPG signal of good quality with the enhanced signal component.

Hereinafter, with reference to FIG. 17, a user interface provided by an electronic device so as to be displayed on a display to acquire a PPG signal according to another embodiment will be described.

Figure 17:
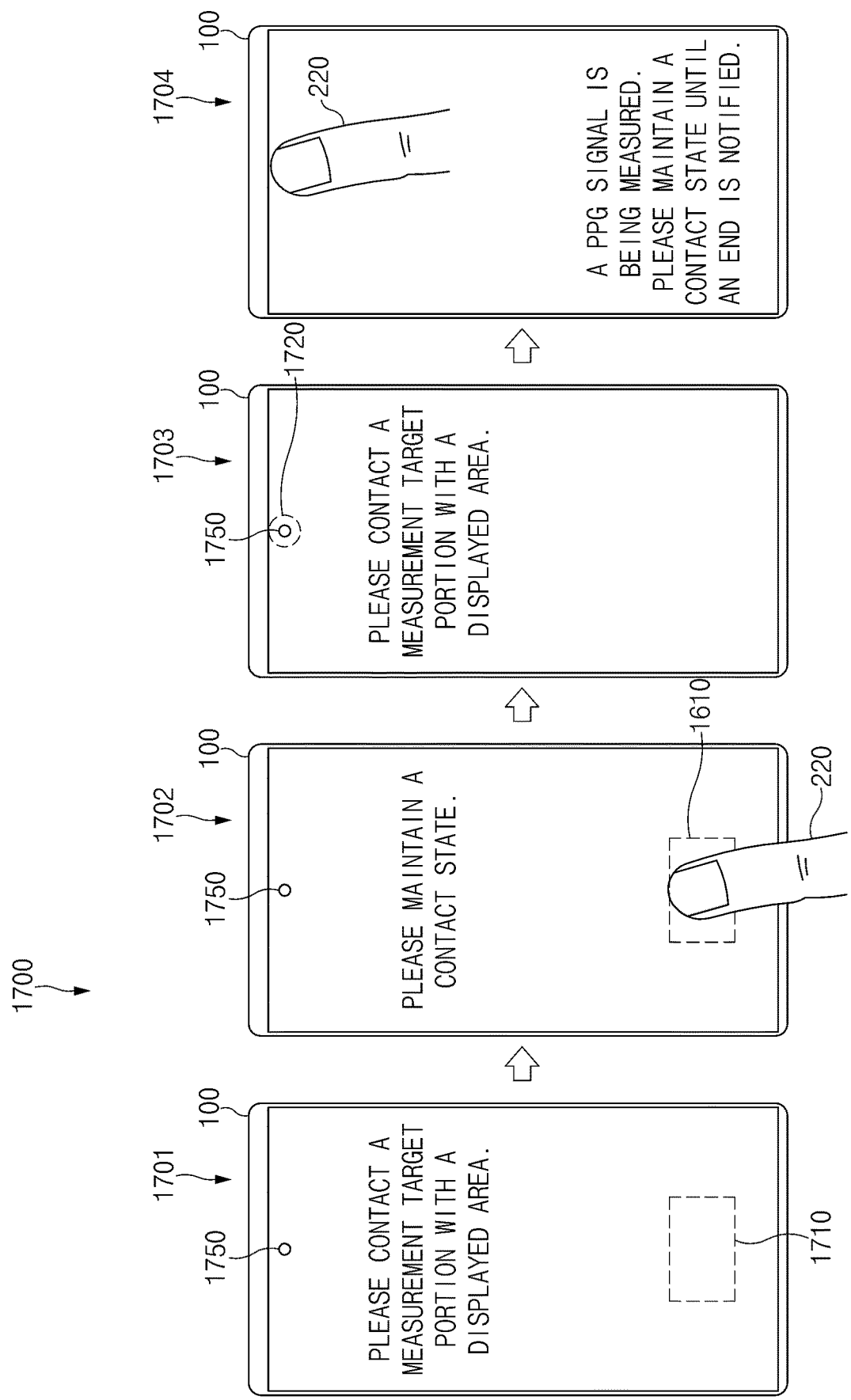
FIG. 17 is a diagram illustrating a user interface provided by an electronic device to acquire a PPG signal according to an embodiment of the disclosure.

FIG. 17 is a diagram 1700 illustrating a user interface provided by an electronic device to acquire a PPG signal according to an embodiment of the disclosure. According to an embodiment of the disclosure, the electronic device 100 of FIG. 16 may be the electronic device 100 of FIG. 1.

Referring to a first state 1701 of FIG. 17, according to an embodiment of the disclosure, the electronic device 100 may display the first area 1710 on the display. The first area 1710 may be displayed so that the user may recognize the first area as being distinguished from other areas on the display. The first area 1710 may be displayed on the display when the electronic device 100 receives a user's input for executing an application for measuring the PPG signal.

The first area 1710 may mean an area displayed on the display in order for the electronic device 100 to emit the ultrasonic waves to the object. The first area 1710 may correspond to an area in which a touch sensor (e.g., a touch panel) corresponding to an ultrasonic device (e.g., the ultrasonic device 110 of FIG. 1) of the electronic device 100 is disposed. According to an embodiment of the disclosure, the electronic device may detect the object in contact with the first area 1710, and, upon detecting the object, may emit the ultrasonic waves to the object using the ultrasonic device. According to an embodiment of the disclosure, when the ultrasonic device is included in a fingerprint recognition sensor, the first area 1710 may be a fingerprint recognition area.

According to an embodiment of the disclosure, in the first state 1701, the electronic device 100 may display the first area 1710 on the display and, at the same time, may display a guide message saying "Please contact a measurement target portion with a displayed area." on the display.

According to an embodiment of the disclosure, in the first state 1701, the electronic device 100 may detect the object 220 (e.g., a user's finger) which is in contact with at least a portion of the first area 1710. According to an embodiment of the disclosure, upon detecting the object 220, the electronic device 100 may enter a second state 1702.

According to an embodiment of the disclosure, in the second state 1702, the electronic device 100 may emit the ultrasonic waves using the ultrasonic device in response to the detection of the object 220. In this case, the object 220 may be exposed to the ultrasonic waves for a predefined time duration such that the blood vessel inside the object 220 may be expanded. According to an embodiment of the disclosure, the electronic device 100 may display a guide message of "Please maintain a contact state" on the display while emitting the ultrasonic waves.

According to an embodiment of the disclosure, the electronic device 100 may enter a third state 1703 when the emission of the ultrasonic waves for a preset time duration has been completed. According to an embodiment of the disclosure, in the third state 1703, the electronic device 100 may display the second area 1720 on the display. The second area 1720 may be displayed so that the user may recognize the second area as being distinguished from other areas on the display. The second area 1720 may be an object recognition area of the light detector of (e.g., the light detector 143 of FIG. 1) of the PPG sensor (e.g., the PPG sensor 140 of FIG. 1). According to an embodiment of the disclosure, the electronic device 100 may use the image sensor (e.g., a CMOS image sensor of a camera 1750) as the light detector of the PPG sensor. Accordingly, according to an embodiment of the disclosure, the second area 1720 may include an area corresponding to the camera 1750 of the electronic device 100.

According to an embodiment of the disclosure, in the third state 1703, the electronic device 100 may display the second area 1720 on the display, and at the same time, may display a guide message of "Please contact a measurement target portion with a displayed area." on this display.

According to an embodiment of the disclosure, in the third state 1703, the electronic device 100 may detect the object 220 (e.g., a user's finger) which is in contact with at least a portion of the second area 1720. According to an embodiment of the disclosure, upon detecting the object 220, the electronic device 100 may enter a fourth state 1704.

According to an embodiment of the disclosure, in the fourth state 1704, the electronic device 100 may emit light using the light source (e.g., the light source 141 of FIG. 1) in response to the detection of the object 220. According to an embodiment of the disclosure, the light source may be a light source (e.g., OLED) of a display panel corresponding to the second area 1720.

According to an embodiment of the disclosure, in the fourth state 1704, the electronic device 100 may detect the light reflected from the object 220 using a light sensor of the camera 1750. According to an embodiment of the disclosure, the light sensor of the camera 1750 may be a CMOS image sensor.

According to an embodiment of the disclosure, in the fourth state 1704, upon the detection of the object 220, the electronic device 100 may operate the light source (e.g., the OLED around the camera 1750) and the light detector (e.g., the CMOS image sensor of the camera 1750) and at the same time, may display a guide message saying "A PPG signal is being measured. Please maintain a contact state until an end is notified" on the display.

According to an embodiment of the disclosure, the electronic device 100 disclosed in the disclosure may measure the PPG signal using the light source (e.g., OLED) of the display, and the image sensor (e.g., the CMOS image sensor of the camera 1750) even when the PPG sensor is not separately included therein.

According to an embodiment of the disclosure, the electronic device 100 disclosed in the disclosure may sum information of 2D array pixels acquired via the image sensor (e.g., the camera 1750) to acquire the PPG signal. According to an embodiment of the disclosure, the light reflected from the object 220 may be detected in a state in which the blood vessel of the object has been expanded by the ultrasonic waves. Thus, the PPG signal having an increased signal component may be acquired from each of the pixels of the two-dimensional array. Accordingly, when the image sensor of the electronic device 100 according to an embodiment captures an image in a rolling shutter manner, the PPG signal may be acquired by summing pixel values on a row basis of the 2D array. According to an embodiment of the disclosure, summing the pixel values on a row basis may allow a signal processing speed (a sampling rate) to be increased, compared to that in a scheme of summing all pixel values of the two-dimensional array.

Therefore, the electronic device 100 according to an embodiment may also acquire information (e.g., HRV (heart rate variability), SpO$_2$ (transcutaneous oxygen saturation), a blood pressure, or a blood glucose level) that requires a relatively higher readout speed, based on the PPG signal acquired using the light source (e.g., OLED) of the display and the image sensor (e.g., the CMOS image sensor of the camera 1750).

Figure 18:
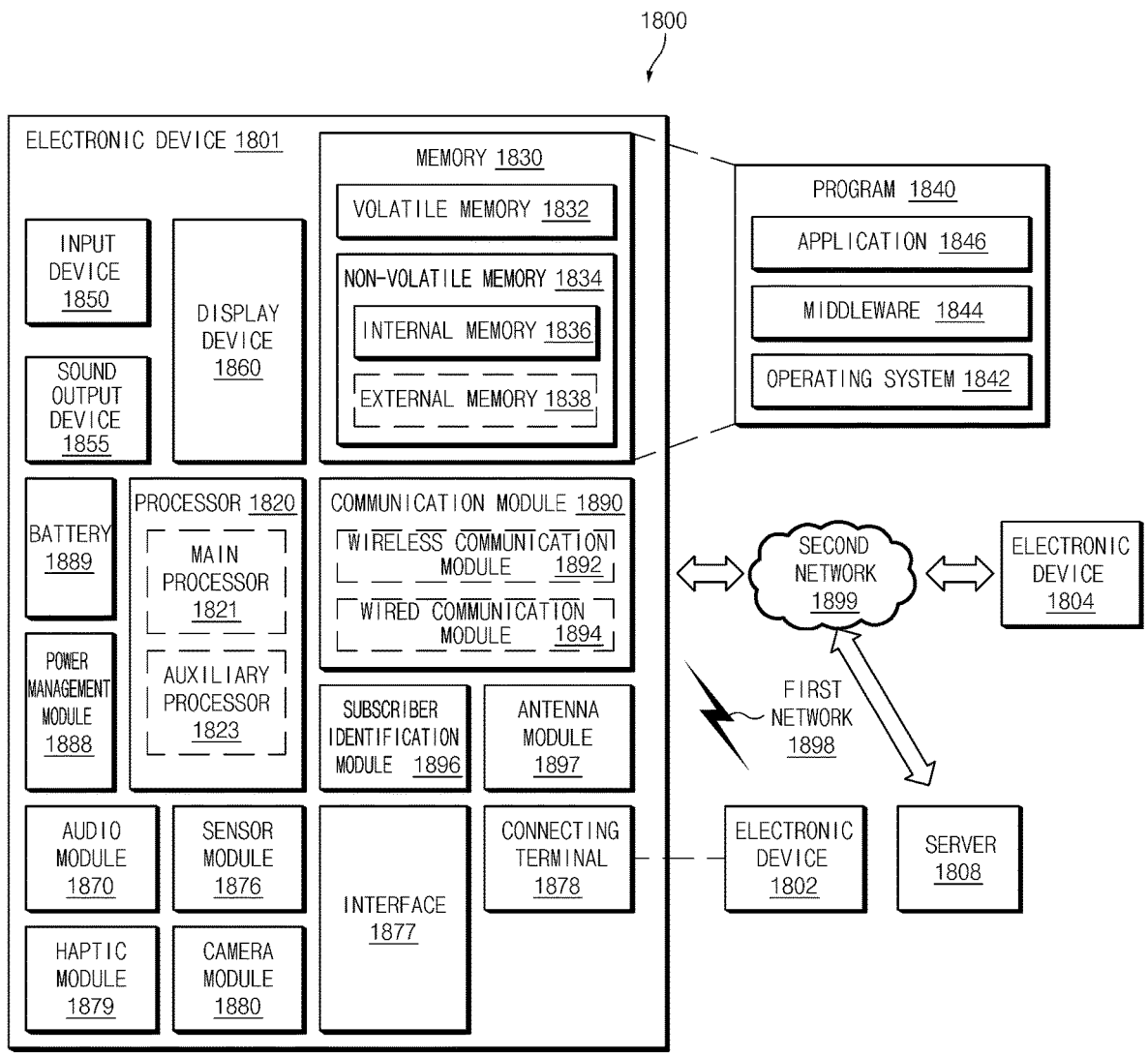
FIG. 18 is a block diagram of an electronic device in a network environment according to an embodiment of the disclosure.

FIG. 18 is a block diagram illustrating an electronic device in a network environment according to an embodiment of the disclosure.

Referring to FIG. 18, an electronic device 1801 in a network environment 1800 may communicate with an external electronic device 1802 via a first network 1898 (e.g., a short-range wireless communication network), or an external electronic device 1804 or a server 1808 via a second network 1899 (e.g., a long-range wireless communication network). According to an embodiment of the disclosure, the electronic device 1801 may communicate with the external electronic device 1804 via the server 1808. According to an embodiment of the disclosure, the electronic device 1801 may include a processor 1820, a memory 1830, an input device 1850, a sound output device 1855, a display device 1860, an audio module 1870, a sensor module 1876, an interface 1877, a haptic module 1879, a camera module 1880, a power management module 1888, a battery 1889, a communication module 1890, a subscriber identification module (SIM) 1896, or an antenna module 1897. In some embodiments of the disclosure, at least one (e.g., the display device 1860 or the camera module 1880) of the components may be omitted from the electronic device 1801, or one or more other components may be added in the electronic device 1801. In some embodiments of the disclosure, some of the components may be implemented as single integrated circuitry. For example, the sensor module 1876 (e.g., a fingerprint sensor, an iris sensor, or an illuminance sensor) may be implemented as embedded in the display device 1860 (e.g., a display).

The processor 1820 may execute, for example, software (e.g., a program 1840) to control at least one other component (e.g., a hardware or software component) of the electronic device 1801 coupled with the processor 1820, and may perform various data processing or computation. According to an embodiment of the disclosure, as at least part of the data processing or computation, the processor 1820 may load a command or data received from another component (e.g., the sensor module 1876 or the communication module 1890) in a volatile memory 1832, process the command or the data stored in the volatile memory 1832, and store resulting data in a non-volatile memory 1834. According to an embodiment of the disclosure, the processor 1820 may include a main processor 1821 (e.g., a central processing unit (CPU) or an application processor (AP)), and an auxiliary processor 1823 (e.g., a graphics processing unit (GPU), an image signal processor (ISP), a sensor hub processor, or a communication processor (CP)) that is operable independently from, or in conjunction with, the main processor 1821. Additionally or alternatively, the auxiliary processor 1823 may be adapted to consume less power than the main processor 1821, or to be specific to a specified function. The auxiliary processor 1823 may be implemented as separate from, or as part of the main processor 1821.

The auxiliary processor 1823 may control at least some of functions or states related to at least one component (e.g., the display device 1860, the sensor module 1876, or the communication module 1890) among the components of the electronic device 1801, instead of the main processor 1821 while the main processor 1821 is in an inactive (e.g., a sleep) state, or together with the main processor 1821 while the main processor 1821 is in an active state (e.g., executing an application). According to an embodiment of the disclosure, the auxiliary processor 1823 (e.g., an image signal processor or a communication processor) may be implemented as part of another component (e.g., the camera module 1880 or the communication module 1890) functionally related to the auxiliary processor 1823.

The memory 1830 may store various data used by at least one component (e.g., the processor 1820 or the sensor module 1876) of the electronic device 1801. The various data may include, for example, software (e.g., the program 1840) and input data or output data for a command related thereto. The memory 1830 may include the volatile memory 1832 or the non-volatile memory 1834.

The program 1840 may be stored in the memory 1830 as software, and may include, for example, an operating system (OS) 1842, middleware 1844, or an application 1846.

The input device 1850 may receive a command or data to be used by other component (e.g., the processor 1820) of the electronic device 1801, from the outside (e.g., a user) of the electronic device 1801. The input device 1850 may include, for example, a microphone, a mouse, a keyboard, or a digital pen (e.g., a stylus pen).

The sound output device 1855 may output sound signals to the outside of the electronic device 1801. The sound output device 1855 may include, for example, a speaker or a receiver. The speaker may be used for general purposes, such as playing multimedia or playing record, and the receiver may be used for an incoming calls. According to an embodiment of the disclosure, the receiver may be implemented as separate from, or as part of the speaker.

The display device 1860 may visually provide information to the outside (e.g., a user) of the electronic device 1801. The display device 1860 may include, for example, a display, a hologram device, or a projector and control circuitry to control a corresponding one of the displays, hologram device, and projector. According to an embodiment of the disclosure, the display device 1860 may include touch circuitry adapted to detect a touch, or sensor circuitry (e.g., a pressure sensor) adapted to measure the intensity of force incurred by the touch.

The audio module 1870 may convert a sound into an electrical signal and vice versa. According to an embodiment of the disclosure, the audio module 1870 may obtain the sound via the input device 1850, or output the sound via the sound output device 1855 or a headphone of an external electronic device (e.g., the external electronic device 1802) directly (e.g., wiredly) or wirelessly coupled with the electronic device 1801.

The sensor module 1876 may detect an operational state (e.g., power or temperature) of the electronic device 1801 or an environmental state (e.g., a state of a user) external to the electronic device 1801, and then generate an electrical signal or data value corresponding to the detected state. According to an embodiment of the disclosure, the sensor module 1876 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1877 may support one or more specified protocols to be used for the electronic device 1801 to be coupled with the external electronic device (e.g., the external electronic device 1802) directly (e.g., wiredly) or wirelessly. According to an embodiment of the disclosure, the interface 1877 may include, for example, a high definition multimedia interface (HDMI), a universal serial bus (USB) interface, a secure digital (SD) card interface, or an audio interface.

A connecting terminal 1878 may include a connector via which the electronic device 1801 may be physically connected with the external electronic device (e.g., the external electronic device 1802). According to an embodiment of the disclosure, the connecting terminal 1878 may include, for example, a HDMI connector, a USB connector, a SD card connector, or an audio connector (e.g., a headphone connector).

The haptic module 1879 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 1879 may include, for example, a motor, a piezoelectric element, or an electric stimulator.

The camera module 1880 may capture a still image or moving images. According to an embodiment of the disclosure, the camera module 1880 may include one or more lenses, image sensors, image signal processors, or flashes.

The power management module 1888 may manage power supplied to the electronic device 1801. According to an embodiment of the disclosure, the power management module 1888 may be implemented as at least part of, for example, a power management integrated circuit (PMIC).

The battery 1889 may supply power to at least one component of the electronic device 1801. According to an embodiment of the disclosure, the battery 1889 may include, for example, a primary cell which is not rechargeable, a secondary cell which is rechargeable, or a fuel cell.

The communication module 1890 may support establishing a direct (e.g., wired) communication channel or a wireless communication channel between the electronic device 1801 and the external electronic device (e.g., the external electronic device 1802, the external electronic device 1804, or the server 1808) and performing communication via the established communication channel. The communication module 1890 may include one or more communication processors that are operable independently from the processor 1820 (e.g., the application processor (AP)) and supports a direct (e.g., wired) communication or a wireless communication. According to an embodiment of the disclosure, the communication module 1890 may include a wireless communication module 1892 (e.g., a cellular communication module, a short-range wireless communication module, or a global navigation satellite system (GNSS) communication module) or a wired communication module 1894 (e.g., a local area network (LAN) communication module or a power line communication (PLC) module). A corresponding one of these communication modules may communicate with the external electronic device via the first network 1898 (e.g., a short-range communication network, such as Bluetooth™, wireless-fidelity (Wi-Fi) direct, or infrared data association (IrDA)) or the second network 1899 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1892 may identify and authenticate the electronic device 1801 in a communication network, such as the first network 1898 or the second network 1899, using subscriber information (e.g., international mobile subscriber identity (IMSI)) stored in the subscriber identification module 1896.

The antenna module 1897 may transmit or receive a signal or power to or from the outside (e.g., the external electronic device) of the electronic device 1801. According to an embodiment of the disclosure, the antenna module 1897 may include an antenna including a radiating element including a conductive material or a conductive pattern formed in or on a substrate (e.g., a printed circuit board (PCB)). According to an embodiment of the disclosure, the antenna module 1897 may include a plurality of antennas. In such a case, at least one antenna appropriate for a communication scheme used in the communication network, such as the first network 1898 or the second network 1899, may be selected, for example, by the communication module 1890 (e.g., the wireless communication module 1892) from the plurality of antennas. The signal or the power may then be transmitted or received between the communication module 1890 and the external electronic device via the selected at least one antenna. According to an embodiment of the disclosure, another component (e.g., a radio frequency integrated circuit (RFIC)) other than the radiating element may be additionally formed as part of the antenna module 1897.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 1801 and the external electronic device 1804 via the server 1808 coupled with the second network 1899. Each of the external electronic devices 1802 and 1804 may be a device of a same type as, or a different type, from the electronic device 1801. According to an embodiment of the disclosure, all or some of operations to be executed at the electronic device 1801 may be executed at one or more of the external electronic devices 1802, 1804, or 1808. For example, if the electronic device 1801 should perform a function or a service automatically, or in response to a request from a user or another device, the electronic device 1801, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1801. The electronic device 1801 may provide the outcome, with or without further processing of the outcome, as at least part of a reply to the request. To that end, a cloud computing, distributed computing, or client-server computing technology may be used, for example.

According to an embodiment disclosed in the disclosure, an electronic device (e.g., the electronic device 100 of FIG. 1 or the electronic device 1801 of FIG. 18) may include a PPG (Photoplethysmography) sensor (e.g., the PPG sensor 140 in FIG. 1, or the PPG sensor 340 in FIG. 3) including a light source (e.g., the light source 141 of FIG. 1) and a light detector (e.g., the light detector 143 in FIG. 1), an ultrasonic device (e.g., the ultrasonic device 110 in FIG. 1), at least one processor (e.g., the processor 120 of FIG. 1) operatively connected to the PPG sensor and the ultrasonic device, and a memory (e.g., the memory 130 of FIG. 1) operatively connected to the at least one processor, wherein the memory may store therein one or more instructions, wherein when the instructions are executed by the at least one processor, the instructions may cause the at least one processor to acquire a PPG signal based on light detected by the light detector, and control an operation of the ultrasonic device based on an indicator value indicating a quality of the PPG signal.

According to an embodiment disclosed in the disclosure, the instructions may cause the at least one processor to sequentially or simultaneously perform an operation of emitting ultrasonic waves using the ultrasonic device and an operation of detecting light using the PPG sensor.

According to an embodiment disclosed in the disclosure, the instructions may cause the at least one processor to, based on determining that the indicator value is greater than or equal to a threshold value, control the ultrasonic device not to emit ultrasonic waves, or based on determining that the indicator value is smaller than the threshold value, control the ultrasonic device to emit ultrasonic waves.

According to an embodiment disclosed in the disclosure, the instructions may cause the at least one processor to, based on determining that the indicator value is greater than or equal to a threshold value, extract at least one of heart rate information, respiration information, stress information, blood pressure information, or blood flow rate information, based on the PPG signal, or based on determining the indicator value is smaller than the threshold value, adjust a power level of an ultrasonic wave emitted from the ultrasonic device.

According to an embodiment disclosed in the disclosure, the instructions may cause the at least one processor to, based on determining that the indicator value is smaller than the threshold value, further adjust an emission time duration of the ultrasonic wave emitted from the ultrasonic device.

According to an embodiment disclosed in the disclosure, the instructions may cause the at least one processor to, based on determining that the indicator value is a first value, control the ultrasonic device to emit an ultrasonic wave having a first ultrasonic wave power level, or based on determining that the indicator value is a second value, control the ultrasonic device to emit an ultrasonic wave having a second ultrasonic wave power level, wherein the second value may be smaller than the first value, and the second ultrasonic wave power level may be greater than the first ultrasonic wave power level.

According to an embodiment disclosed in the disclosure, the instructions may cause the at least one processor to, based on determining that the indicator value is a first value, control the ultrasonic device to emit an ultrasonic wave for a first time duration, or based on determining that the indicator value is a second value, control the ultrasonic device to emit an ultrasonic wave for a second time duration, wherein the second value may be smaller than the first value, and the second time duration may be larger than the first time duration.

According to an embodiment disclosed in the disclosure, the ultrasonic device may be disposed between the light source and the light detector on one face of a display panel (e.g., the display panel 230 in FIG. 2 or the display device 1860 in FIG. 18) of the electronic device.

According to an embodiment disclosed in the disclosure, a center of the ultrasonic device may be positioned at a median point between the light source and the light detector.

According to an embodiment disclosed in the disclosure, the ultrasonic device may include a first ultrasonic wave generator and a second ultrasonic wave generator, wherein the instructions may cause the at least one processor to control the first ultrasonic wave generator to emit a first ultrasonic wave and control the second ultrasonic wave generator to emit a second ultrasonic wave, wherein a phase of the first ultrasonic wave and a phase of the second ultrasonic wave may be in-phase with each other.

According to an embodiment disclosed in the disclosure, the ultrasonic device may include a first ultrasonic wave generator and a second ultrasonic wave generator, wherein the instructions may cause the at least one processor to control the first ultrasonic wave generator to emit a first ultrasonic wave toward a focal point positioned at a medial point between the light source and the light detector, and control the second ultrasonic wave generator to emit a second ultrasonic wave toward the focal point.

According to an embodiment disclosed in the disclosure, the ultrasonic device may include a first ultrasonic wave generator and a second ultrasonic wave generator, wherein the first ultrasonic wave generator and the second ultrasonic wave generator may be arranged such that a focal point of beam forming of a first ultrasonic wave emitted from the first ultrasonic wave generator and a second ultrasonic wave emitted from the second ultrasonic wave generator is positioned at a median point between the light source and the light detector.

According to an embodiment disclosed in the disclosure, a PPG signal acquisition method by an electronic device (e.g., the electronic device 100 in FIG. 1 or the electronic device 1801 in FIG. 18) including an ultrasonic device (the ultrasonic device 110 in FIG. 1) may include, based on detecting an object (e.g., the object 220 in FIG. 2), emitting, by the ultrasonic device, an ultrasonic wave toward the object, based on detecting the object, irradiating, by a light source (e.g., the light source 141 in FIG. 1) included in the electronic device, light toward the object, detecting, by a light detector (e.g., the light detector 143 in FIG. 1) included in the electronic device, light reflected from the object, acquiring a PPG signal based on the detected light, calculating an indicator value indicating a quality of the PPG signal, and controlling an operation of the ultrasonic device based on the indicator value.

According to an embodiment disclosed in the disclosure, the controlling of the operation of the ultrasonic device may include emitting the ultrasonic waves using the ultrasonic device, wherein the PPG signal acquisition method may sequentially or simultaneously perform an operation of emitting the ultrasonic waves and an operation of detecting the light.

According to an embodiment disclosed in the disclosure, the controlling of the operation of the ultrasonic device may include, based on determining that the indicator value is greater than or equal to a threshold value, controlling the ultrasonic device not to emit ultrasonic waves, or based on determining that the indicator value is smaller than the threshold value, controlling the ultrasonic device to emit ultrasonic waves.

According to an embodiment disclosed in the disclosure, the PPG signal acquisition method may include, based on determining that the indicator value is greater than or equal to a threshold value, extracting at least one of heart rate information, respiration information, stress information, blood pressure information, or blood flow rate information, based on the PPG signal, or based on determining the indicator value is smaller than the threshold value, adjusting a power level of an ultrasonic wave emitted from the ultrasonic device.

According to an embodiment disclosed in the disclosure, the PPG signal acquisition method may include, based on determining that the indicator value is smaller than the threshold value, further adjusting an emission time duration of the ultrasonic wave emitted from the ultrasonic device.

According to an embodiment disclosed in the disclosure, the adjusting of the power level of the ultrasonic wave may include, based on determining that the indicator value is a first value, controlling the ultrasonic device to emit an ultrasonic wave having a first ultrasonic wave power level, or based on determining that the indicator value is a second value, controlling the ultrasonic device to emit an ultrasonic wave having a second ultrasonic wave power level, wherein the second value may be smaller than the first value, and the second ultrasonic wave power level may be greater than the first ultrasonic wave power level.

According to an embodiment disclosed in the disclosure, the PPG signal acquisition method may further include displaying a first area on a display (e.g., the display panel 230 in FIG. 2 or the display device 1860 in FIG. 18) of the electronic device based on an application for measuring the PPG signal being executed in response to reception of an input from a user, wherein the ultrasonic device may emit the ultrasonic wave based on detection that the object is in contact with at least a portion of the first area.

According to an embodiment disclosed in the disclosure, the PPG signal acquisition method may further include displaying a second area on the display prior to the irradiating of the light, wherein the light source may irradiate the light based on detection that the object is in contact with at least a portion of the second area.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B", "at least one of A and B", "at least one of A or B", "A, B, or C", "at least one of A, B, and C", and "at least one of A, B, or C" may include any one of, or all possible combinations of the items enumerated together in a corresponding one of the phrases. As used herein, such terms as "1st" and "2nd", or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic", "logic block", "part", or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 1840) including one or more instructions that are stored in a storage medium (e.g., an internal memory 1836 or an external memory 1838) that is readable by a machine (e.g., the electronic device 1801). For example, a processor (e.g., the processor 1820) of the machine (e.g., the electronic device 1801) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a photoplethysmography (PPG) sensor including a light source and a light detector;
an ultrasonic device;
memory storing one or more computer programs; and
one or more processors communicatively coupled to the PPG sensor, the ultrasonic device and the memory,
wherein one or more computer programs include computer-executable instructions that, when executed by the one or more processors individually or collectively, cause the electronic device to:
measure, based on a first PPG signal acquired based on light detected by the light detector, a quality of the first PPG signal, the quality of the first PPG signal expressed as a ratio of an alternate current (AC) component of the first PPG signal and a direct current (DC) component of the first PPG signal,
determine whether an indicator value indicating the quality of the first PPG signal is smaller than a threshold value,
based on determining that the indicator value is smaller than the threshold value, control an operation of the ultrasonic device, and
obtain biometric information based on a second PPG signal acquired after the operation of the ultrasonic device is controlled.

2. The electronic device of claim 1, wherein the one or more computer programs further include computer-executable instructions that, when executed by the one or more processors individually or collectively, cause the electronic device to sequentially or simultaneously perform an operation of emitting ultrasonic waves using the ultrasonic device and an operation of detecting light using the PPG sensor.

3. The electronic device of claim 1, wherein the one or more computer programs further include computer-executable instructions that, when executed by the one or more processors individually or collectively, cause the electronic device to:
based on determining that the indicator value is greater than or equal to the threshold value, control the ultrasonic device not to emit ultrasonic waves.

4. The electronic device of claim 1, wherein the biometric information includes at least one of heart rate information, respiration information, stress information, blood pressure information, or blood flow rate information.

5. The electronic device of claim 1, wherein the one or more computer programs further include computer-executable instructions that, when executed by the one or more processors individually or collectively, cause the electronic device to:
based on determining that the indicator value is smaller than the threshold value, adjust at least one of an emission time duration of an ultrasonic wave emitted from the ultrasonic device and a power level of the ultrasonic wave emitted from the ultrasonic device.

6. The electronic device of claim 5,
wherein the one or more computer programs further include computer-executable instructions that, when executed by the one or more processors individually or collectively, cause the electronic device to:
based on determining that the indicator value is a first value, control the ultrasonic device to emit the ultrasonic wave having a first ultrasonic wave power level, or
based on determining that the indicator value is a second value, control the ultrasonic device to emit the ultrasonic wave having a second ultrasonic wave power level, and
wherein the second value is smaller than the first value, and the second ultrasonic wave power level is greater than the first ultrasonic wave power level.

7. The electronic device of claim 5,
wherein the one or more computer programs further include computer-executable instructions that, when executed by the one or more processors individually or collectively, cause the electronic device to:
based on determining that the indicator value is a first value, control the ultrasonic device to emit an ultrasonic wave for the emission time duration, or
based on determining that the indicator value is a second value, control the ultrasonic device to emit an ultrasonic wave for a second time duration, and
wherein the second value is smaller than the first value, and the second time duration is larger than the emission time duration.

8. The electronic device of claim 1, wherein the ultrasonic device is disposed between the light source and the light detector on one face of a display panel of the electronic device.

9. The electronic device of claim 1, wherein a center of the ultrasonic device is positioned at a median point between the light source and the light detector.

10. The electronic device of claim 9,
wherein the ultrasonic device includes a first ultrasonic wave generator and a second ultrasonic wave generator, wherein the one or more computer programs further include computer-executable instructions that, when executed by the one or more processors individually or collectively, cause the electronic device to:
control the first ultrasonic wave generator to emit a first ultrasonic wave, and
control the second ultrasonic wave generator to emit a second ultrasonic wave, and
wherein a phase of the first ultrasonic wave and a phase of the second ultrasonic wave are in-phase with each other.

11. The electronic device of claim 1,
wherein the ultrasonic device includes a first ultrasonic wave generator and a second ultrasonic wave generator, and
wherein the one or more computer programs further include computer-executable instructions that, when executed by the one or more processors individually or collectively, cause the electronic device to:
control the first ultrasonic wave generator to emit a first ultrasonic wave toward a focal point positioned at a medial point between the light source and the light detector, and
control the second ultrasonic wave generator to emit a second ultrasonic wave toward the focal point.

12. The electronic device of claim 1,
wherein the ultrasonic device includes a first ultrasonic wave generator and a second ultrasonic wave generator, and
wherein the first ultrasonic wave generator and the second ultrasonic wave generator are arranged such that a focal point of beam forming of a first ultrasonic wave emitted from the first ultrasonic wave generator and a second ultrasonic wave emitted from the second ultrasonic wave generator is positioned at a median point between the light source and the light detector.

13. A photoplethysmography (PPG) signal acquisition method performed by an electronic device including an ultrasonic device and a PPG sensor, the method comprising:
acquiring, by the electronic device, a first PPG signal based on light detected using the PPG sensor;
measuring, by the electronic device, based on the first PPG signal, a quality of the first PPG signal, the quality of the first PPG signal expressed as a ratio of an alternate current (AC) component of the first PPG signal and a direct current (DC) component of the first PPG signal;
determining, by the electronic device, whether an indicator value indicating the quality of the first PPG signal is smaller than a threshold value;
based on determining that the indicator value is smaller than the threshold value, controlling, by the electronic device, an operation of the ultrasonic device; and
obtaining biometric information based on a second PPG signal acquired after the operation of the ultrasonic device is controlled.

14. The method of claim 13,
wherein the PPG signal acquisition method further comprises displaying a first area on a display of the electronic device based on an application for measuring the first PPG signal being executed in response to reception of an input from a user, and
wherein the ultrasonic device emits an ultrasonic wave based on detection that an object is in contact with the display in an area corresponding to at least a portion of the displayed first area.

15. The method of claim 14,
wherein the PPG signal acquisition method further comprises displaying a second area on the display, and wherein the PPG sensor acquires the first PPG signal based on detection that the object is in contact with an area of the display corresponding to at least a portion of the displayed second area.

* * * * *